United States Patent [19]
Vallee et al.

[11] Patent Number: 4,966,849
[45] Date of Patent: Oct. 30, 1990

[54] CDNA AND GENES FOR HUMAN ANGIOGENIN (ANGIOGENESIS FACTOR) AND METHODS OF EXPRESSION

[75] Inventors: Bert L. Vallee, Brookline, Mass.; Kotoku Kurachi, Ann Arbor, Mich.

[73] Assignee: President and Fellows of Harvard College, Cambridge, Mass.

[21] Appl. No.: 305,968

[22] Filed: Feb. 2, 1989

Related U.S. Application Data

[63] Continuation-in-part of Ser. No. 105,106, Oct. 5, 1987, abandoned, which is a continuation of Ser. No. 778,547, Sep. 20, 1985, Pat. No. 4,721,672.

[51] Int. Cl.$^5$ .................. C12N 9/22; C12N 15/00; C07K 3/00; C07H 15/12
[52] U.S. Cl. ........................... 435/199; 435/172.3; 435/240.25; 435/252.3; 435/320; 530/399; 536/27; 935/13; 935/14; 935/28; 935/29; 935/70; 935/71; 935/73
[58] Field of Search ................. 530/399; 435/172.3, 435/199, 252.3, 320; 536/27; 935/28, 29, 32, 13, 14, 70, 71, 73

[56] References Cited

U.S. PATENT DOCUMENTS

| | | | |
|---|---|---|---|
| 4,229,531 | 10/1980 | Tolbert et al. | 435/4 |
| 4,503,038 | 3/1985 | Banda et al. | 424/95 |
| 4,721,672 | 1/1988 | Vallee et al. | 435/70 |
| 4,727,137 | 2/1988 | Vallee et al. | 530/412 |

FOREIGN PATENT DOCUMENTS

| | | |
|---|---|---|
| 0117060 | of 0000 | European Pat. Off. |
| 0198415A2 | of 0000 | European Pat. Off. |
| 3716722.7 | of 0000 | Fed. Rep. of Germany |

OTHER PUBLICATIONS

Holmes et al., *Cell* 32:1029–1032 (1983).
Brosius et al., *J. Mol. Biol.* 148:107–127 (1981).
Maniatis et al. In *Molecular Cloning, a Laboratory Manual*. Cold Spring Harbor, (1982), pp. 405–410.
Battersby, T., Plating of Mandibular Fractures, British J. Oral Surg., 194–201 (no date).
J. Natl. Cancer Inst. 41:111–124 (1968 Greenblatt and Shubik).
Auerbach, in *Lymphokines*, Pick and Landy, etd. 69–88, Academic Press, New York, 1981.
Invest. Opthalm. Vis. Sci. 22:191–199 (1982, Berman et al.).
J. Natl. Cancer Inst. 69:1183–1188 (1982, Raju et al.).
Proc. Natl. Acad. Sci. USA 79: 7773–7777 (1982, Banda et al.).
Proc. Natl. Acad. Sci. USA 78: 3068–3072 (1981, D'Amore et al.).
J. Exp. Med. 133: 275–288 (1971, Folkman et al.).
Biochemistry 12: 3159–3165 (1973, Tuan et al.).
Int. J. Cancer 23: 82–88 (1979, Phillips and Kumar).
Ewers, R., Experimental and Clinical Results of New Advances in the Treatment of Facial Trauma, Plastic and Reconstructive Surg., 25–31 (Jan. 1985).
Br. J. Cancer 40: 493–496 (1979, Weiss et al.).
J. Biol. Chem. 256: 9605–9611 (1981, Fenselau et al.).
Int. J. Cancer 32: 461–464 (1983, Kumar et al.).
Experientia 41: 1–15 (1985, Vallee et al.).
Jones, R., Military Orthopedic Surgery, Surgery, Its Principles and Practice, pp. 624–675 (1909 Saunders).
Biochemistry 24: 5480–5486 (1985, Fett et al.).

(List continued on next page.)

*Primary Examiner*—Thomas D. Mays
*Attorney, Agent, or Firm*—Allegretti & Witcoff, Ltd.

[57] ABSTRACT

DNA sequences encoding a protein having angiogenic activity and mutated DNA sequences encoding a protein having decreased angiogenic activity are disclosed. Expression vectors containing these wild-type or mutated sequences are introduced into host cells and direct the production of wild-type or mutant angiogenic proteins. Proteins produced according to the invention are useful in the diagnosis of malignancies, for promoting wound healing, and for other diagnostic and therapeutic purposes. Mutant proteins produced according to the invention are useful therapeutic compositions as angiogensis inhibitors, which may retard tumor growth by inhibiting the development of a hemovascular network.

22 Claims, 9 Drawing Sheets

OTHER PUBLICATIONS

Biochemistry 25: 3527–3532 (1986, Shapiro et al.).
Gene 56: 61–70 (1987, Denefel et al.).
Biochemistry 24: 5486–5494 (1985, Strydom et al.).
FASEB Abstract #4309, 61st Annual Meeting, Chicago, 1977 (Rettura et al.).
Cancer Res. 36: 110–114 (1976, Klagsbrun et al.).
Science 195: 880–881 (1977, Brem et al.).
Br. J. Cancer 35: 347–356 (1977, Knighton et al.).
Nature 263: 797–800 (1976, Langer and Folkman).
Proc. Natl. Acad. Sci. USA 76: 4350 (1979, Towbin et al.).
Proc. Natl. Acad. Sci. USA 82: 488–494 (1985, Kunkel).
Proc. Natl. Acad. Sci. 74: 5463–5467 (1977, Sanger et al.).
Roed–Petersen, B., Absorbable Synthetic Suture Material for Internal Fixation of Fractures of the Mandible, 3 Int. J. Oral Surg., 133–36 (1974).
The EMBO Journal 4: 519–526 (1985, McCarthy et al.).
Gene 41: 201–206 (1986, McCarthy et al.).
Biochemistry 26: 5141–5146 (1987, Shapiro et al.).
Methods in Enzymology 101: 155–164 (1983, Nicholas and Yanofsky).
Gene 2: 95–113 (1977, Bolivar et al.).
Methods in Enzymology 101: 20–78 (1983, Messing).
Gene 19: 259–268 (1982, Viera and Messing).
Nature 275: 104–108 (1978, Beggs).
Gene 8: 121–133 (1979, Broach et al.).
J. Biol. Chem. 255: 12073–12080 (1980, Hiteman et al.).
J. Mol. Appl. Genet. 1: 419–434 (1982, Alber and Kawasaki).
Cell 30: 933–943 (1982, Kurtan and Herskowitz).
Science 222: 809–814 (1983, Palmiter et al.).
Cell 15: 687–701 (1978, Maniatis et al.).
J. Mol. Biol. 113: 237–251 (1977, Rigby et al.).
Science 196: 180–182 (1977, Benton and Davis).
Nucleic Acids Res. 9: 309–321 (1981, Messing et al.).
Gene 26: 101–106 (1983, Norrander et al.).
Proc. Natl. Acad. Sci. USA 79: 4298–4302 (1982, Poncz et al.).
Methods in Enzymology 100: 60–97 (1983, Guo and Wu).
Science 216: 1065–1070 (1982, Schmid and Jelineck).
Nature 263: 211–214 (1976, Proudfoot and Brownlee).
Thrombosis and Hemostasis 54: 282 (1985, Kurachi and Palmiter).
Anal. Biochem. 131: 385–393 (1983, Durnam and Palmiter).
Cell 19: 753–764 (1980, Nasmyth and Tatchell).
Proc. Natl. Acad. Sci. USA 84: 4767–4771 (1987, Tabor and Richardson).
J. Biol. Chem. 254: 12484–124876 (1979, Blackburn).
Proc. Natl. Acad. Sci. 84: 2238–2241 (1987, Shapiro and Vallee).
Fogh and Trempe, in *Human Tumor Cells in Vitro*, Fogh ed., 115–160, Plenum, New York, 1975.
Biochemistry 27: 219–226 (1987, Harper et al.).
J. Chromatography 336: 93–104 (1984, Bidlingmeyer et al.)
Methods in Enzymology 154: 367–382 (1987, Kunkel et al.)

Fig. 1

1
<Glu-Asp-Asn-Ser-Arg-Tyr-Thr-His-Phe-Leu-Thr-Gln-His-Tyr-Asp-15
Ala-Lys-Pro-Gln-Gly-Arg-Asp-Asp-Arg-Tyr-Cys-Glu-Ser-Ile-Met-30
Arg-Arg-Arg-Gly-Leu-Thr-Ser-Pro-Cys-Lys-Asp-Ile-Asn-Thr-Phe-45
Ile-His-Gly-Asn-Lys-Arg-Ser-Ile-Lys-Ala-Ile-Cys-Glu-Asn-Lys-60
Asn-Gly-Asn-Pro-His-Arg-Glu-Asn-Leu-Arg-Ile-Ser-Lys-Ser-Ser-75
Phe-Gln-Val-Thr-Thr-Cys-Lys-Leu-His-Gly-Gly-Ser-Pro-Trp-Pro-90
Pro-Cys-Gln-Tyr-Arg-Ala-Thr-Ala-Gly-Phe-Arg-Asn-Val-Val-Val-105
Ala-Cys-Glu-Asn-Gly-Leu-Pro-Val-His-Leu-Asp-Gln-Ser-Ile-Phe-120
123
Arg-Arg-Pro-OH.

Fig. 3

```
-600  TGTTTTATT TTTTTCCGAG ACGGAGTCTC GCTCTGTCGC CAAGGCTGGA GTGCAGTGGA GCGATCTCGG CTCACTGCAA GCTCCGCCTC CCGGGTTCAG
-500  GCCATCTCC TGCCTCAGCC TCCCAAGTAG CTGGGACTAC AGGCGCCCGC CTGGGACTAC AGGCGCCCGC GCTAATTTTT TGTATTTTTA GTAGAGACGG GGTTTCACCG
-400  TGGTAGCCAG GATGGTCTCG ATCTCCTGAC CTCGTGATCC GCCCGCCTTG TGGTACCCAG TAGAGCCTA GTGCTGGGAT TACAGGCGTG AGACCGCGCC CGGCCGTCAT
-300  TTGGTATGTC TTAAATGTGCC TCAGGACCTA GCACAGTCCC TGGTACCCAG TAGAGCCTA GTTATCAAT GTTATGTTC GTTATCAAT AATAAATACA TGAATTAAAG
-200  AGTAGAGTG GATTTTGTAA TGTTACGACT GATAGAGAAA TTCTAAGGGA TACTCAGTGA TGGGGAAGAA CGGTTGGAGC TAGAGGTTGT GCTCAGGAAA
-100  CTATTAAATA GACGTTCCGC AGGAAGGGAT TGAGGTTAAT GAGGTTAAT GAGGAAGGGA AAATAGAATA TAAATTTGG TGGTGGAAAA GATCTGATTC
  -1  ATGATGCCGT GTCAGAGAGC AAAGCTCCTG TCCTTTTGGC CTAATTTGGT GATCTGTGTC TTGGGCCTA CACACCTCCT TTTGCCCTCC GCAGGAGCCT
       ↓ -24        MetVal  MetGlyLeuGly ValLeuLeuVal PheValLeuLeu ThrGlnHis TyrAspAlaLys ProGlnGlyArg AspAspArg TyrCysGlu
 101  GTGTTGGAAG AG ATG GTG ATG GGC CTG GGC GTG CTC CTG GTT TTG TTG ACA CAC CAG CAC TAT GAT GCC AAA CCA CAG GGC CGG GAT GAC AGA TAC TGT GAA
       +1                                                            10                                       20
      GlnAspAsnSer ArgTyrThrHis PheLeuThrLeu ThrLeuThrLeu
 185  CAG GAT AAC TCC AGG TAC ACA CAC TTC CTG ACC CTG ACC
       30                                                             40                                       50
      SerIleMet ArgArgArgGly LeuThrSerPro CysLysAsp IleAsnThrPhe IleHisGly AsnLysArg SerIleLys
 266  AGC ATC ATG AGG AGA CGG GGT CTG ACC TCA CCC TGC AAA GAC ATC AAC ACA TTT ATT CAT GGC AAC AAG CGC AGC ATC AAG
       60                                                             70                                       80
      AlaIleCys GluAsnLysAsn GlyAsnProHis ArgGluGlu AsnLeuArgIle SerLysLys SerSerPhe GlnValThr ThrCys
 347  GCC ATC TGT GAA AAC AAG AAT GGA AAC CCT CAC AGA GAA AAC CTA AGA ATA AGC AAG TCT TCT TTC CAG GTC ACC ACT TGC
       90                                                            100
      LysLeuHis GlySerProPro TrpProPro Cys GlnTyrArg AlaThrAla GlyPheArg AsnValVal AlaCysGlu
 428  AAG CTA CAT GGT TCC CCT CCA TGG CCT CCA TGC CAG TAC CGA GCC ACA GCG GGG TTC AGA AAC GTT GTT GCT TGT GAA
      110                         120        123
      AsnGlyLeuPro ValHisLeu AspGlnSerIle PheArg ArgPro STOP
 509  AAT GGC TTA CCT GTC CAC TTG GAT CAG TCA ATT TTC CGT CCG TAA CCAGCGGGCC CCTGGTCAAG TGCTGGCTCT GCTGTCCTTG
```

Fig. 3 CONT'D.

```
 597  CCTTCCATTT CCCCTCTGCA CCAGAACAG  TGGTGGCAAC ATCCATGCC  AAGGGCCCAA AGAAAGAGCT ACCTGGACCT TTTGTTTCT  GTTTGACAAC
 697  ATGTTAATA  AATAAAAATG TCTTGATATC AGTAAGAATC AGAGTCTTCT CACTGATTCT TTTTTTTTT  GGGCATATTG ATCTTCCCC  CATTTCTCT  ACTTGGCTGC
 797  TCCTGAGAG  GACTGCATAG GATAGAAATG CCTTTTTCTT TTCTTTTCGT TTTTTTTTT  GAGATGGAGT TTCACTCTGT CGCCCAGGCT
 897  TAAGTGCAAT GGCACAATCT CGGCTCACTG CAACCTCTCT CTCCTGGGT  CAGTGATTC  GCCTCCCAAA TCCTGCCTCA TAGCTGAGAT TACAGGCATG
 997  CACCACCACA CCTGGCTAAT TTTTGTGTTT TTAGTAGAGA CAGGGTTTCA CCGTTTTGGC CAGGTTGGTC TTGAACTCCT GACCTCGGGA GATCCGCCCA
1097  CCTTGGCCTC TCTTTGTGCT GGGATTACAG GCATGAGCCA CTCAGCCGGG CCACTTTTC  AGTTTTTACA AGTCATTAGG GAGGTAGACT
1197  TTACCTCTCT GTGAAGGAAA GTATGGTATG TTGATCTACA GAGAGAGATG GAAAAATTCC AGGGCTCGTA GCTACTAAGC AGAATTCCA  AGATAGGCAA
1297  ATGTTTTTT  CTGTCAAATA ATAAGCTAAT ATTACTTCTA CAAATATGAG ACCTTGGAGA GAAGTTCCA  AGGACCAAGT ACCAACATAC CAACAGATTA
1397  TTATAGTTTC TCTCACTCTT ACACACACAC ACACATATAT AATACCAGCAT AATCCAGAAA ATCATTCAG  GGTAGCCACC TTTTGTCTTA
1497  ATCGAGAGAT AATTTTGATG TTTGAATGGA ATGCTCCCAG GATATTCTCT TGTCATGGTT ATTTATATA  AAATTCAAAA ACCAATTACA TTATTCCTC
1597  TGTAATCTTT TACTTTATCA ACTAATGTCT GGCAAGTGTG GAAGTTATAG AAGATTCCGG ACATGGTGAA ATCTCACGCT TGTAATCCAG
1697  CACTTTGGGA AGCTGAGGCG GAGGTCAAGA GATCAAGACC GGAGGCTGAG ATCCTGAACC CGCTTGAACC TAGGAGGCGG AGTTGCACT  GTGAAAATTA
1797  GCTGGGCGTG GTGGCACACA CCTATAGTCC CAGCTACTCG GCAGGAGAAT GCAGGAGAAT CGCTTGAACC TAGGAGGCGG AGTTGCACT  GAGCCGAGAT
1897  CACGCCACTG CACTCCAGCC TGGGCGACAG AGCGAGACTC CATCTCAAAA AAAAAAAAA  AATGAAGATC CCAGTTTATC CCAGTTTATC  CCTTATTCTT
1997  CCTCAATTCT CAAGATTGT  TTTAAGTTA  ACATAACTTA GGTAACACA  CTCTTTGTAA AATACACTGT TCAATCTACA GACTCAGTGG TTAGCTTCCT
2097  GTTAACTAAT TTCTGTTGAC AGGTACTGG  ATATTTATT  TAGAAAGTGG TTGCCAATAA ATTAGTTATA AGTCGCCAGT TTCACTGCCT TGTGAACACA
2197  TAAGTATTGT GGTCTCAGTA TTCCCTATGG TGGCTTCTCC TGCTCCTGGT ATGCCCTGA  AATGGGCCAA AAGCCGTGGC TCCCAATGC  TCAGGTTATA
2297  GAACATTGTC CAGGTACCAC CTAGGAGAGC CCAGCCTCAC TGAAAGTATT CAAATTTAGG AATGGGTTG  AGAAGTAGGT AGCTGGTATG TGCTTAGCAC
2397  AAGAATCTCT CTTCCTTGGG TTAGTCTGTT TCAAAACTGA AAACACTGTC AAAATAGGAA AAAGTATTCC AACCTCTGT  CACTAGAAAA
```

```
          SphI        XhoI                                          1a
          ┌──┐        ┌───┐
        His Met Gln Asp Asn Ser Arg Tyr Thr His Phe Leu Thr Gln His Tyr Asp Ala Lys Pro Gln
      C CAC ATG CAG GAC AAC TCG AGG TAT ACA CAT TTC CTG ACC CAG CAC TAT GAC GCT AAA CCG CAG
     GT ACG GTC CTG CTG TTG AGC TCC ATA TGT GTA AAG GAC TGG GTC GTG ATA CTG CGA TTT GGC GTC
                                                 1b                                      2b
                   PvuI       2a                                SpeI          3a       EcoRV
                   ┌──┐                                         ┌───┐
        Gly Arg Asp Asp Arg Tyr Cys Glu Ser Ile Leu Arg Arg Arg Gly Leu Thr Ser Pro Cys Lys Asp Ile
        GGC CGG GAC GAT CGT TAC TGC GAA TCG ATT CTG AGA CGT CGT GGG TTA ACT AGT CCG TGC AAA GAT ATC
        CCG GCC CTG CTA GCA ATG ACG CTT AGC TAA GAC TCT GCA GCA CCC AAT TGA TCA GGC ACG TTT CTA TAG
             3a                                  2b                                            3b
                                                          NdeI
                                                          ┌──┐
        Asn Thr Phe Ile His Gly Asn Lys Arg Ser Ile Lys Ala Ile Cys Glu Asn Lys Gly Asn Pro His
        AAC ACT TTC ATC CAT GGT AAC AAG CGT TCT ATC AAA GCC ATA TGC GAA AAC AAA GGT AAC CCG CAT
        TTG TGA AAG TAG GTA CCA TTG TTC GCA AGA TAG TTT CGG TAT ACG CTT TTG TTT CCA TTG GGC GTA
                    4a        BspMI                    3b                                  4b
                              ┌───┐
        Arg Glu Asn Leu Arg Ile Ser Lys Ser Ser Phe Gln Val Thr Thr Cys Lys Leu His Gly Gly Ser Pro
        CGC GAA AAC CTG CGC ATC AGC AAG TCA AGC TTC CAG GTT ACA ACT TGC AAA CTT CAT GGG GGA TCC CCG
        GCG CTT TTG GAC GCG TAG TCG TTC AGT TCG AAG GTC CAA TGT TGA ACG TTT GAA GTA CCC CCT AGG GGC
                    5a                          4b                                          5b
                                      NaeI
                                      ┌───┐
        Trp Pro Pro Cys Gln Tyr Arg Ala Thr Ala Gly Phe Arg Asn Val Val Ala Cys Glu Asn Gly Leu
        TGG CCG CCA TGC CAG TAC CGT GCT ACT GCC GGC TTC CGT AAT GTT GCT TGT GAA AAC GGT CTG
        ACC GGC GGT ACG GTC ATG GCA CGA TGA CGG CCG AAG GCA TTA CAA CGA CAC CTT TTG CCA GAC
             6a                                  5b                                      6b
            XbaI                                        EcoRI
            ┌───┐                                       ┌───┐
        Pro Val His Leu Asp Gln Ser Ile Phe Arg Arg Pro --- ---
        CCA GTC CAT CTA GAT CAG TCT ATC TTC CGA AGG CCT TAA TAG
        GGT CAG GTA GAT CTA GTC AGA TAG AAG GCT TCC GGA ATT ATC TTA A
                    6b
```

Fig. 7

CDNA AND GENES FOR HUMAN ANGIOGENIN (ANGIOGENESIS FACTOR) AND METHODS OF EXPRESSION

This application is a continuation-in-part of pending U.S. Pat. application Ser. No. 105,106, filed Oct. 5, 1987, now abandoned, which is a continuation of Ser. No. 778,547, filed Sept. 20, 1985, now U.S. Pat. No. 4,721,672.

FIELD OF THE INVENTION

This invention relates to protein production through recombinant DNA techniques. More particularly, it relates to DNA sequences encoding proteins having angiogenic activity and to methods of expressing those sequences.

This invention further relates to mutant angiogenin genes produced by site-specific mutagenesis and recombinant DNA techniques and includes DNA sequences for the mutant angiogenin genes which encode mutant proteins with altered angiogenic and ribonucleolytic activities. Specifically, the invention relates to methods of expression of mutant angiogenin proteins with decreased angiogenic and ribonucleolytic activities as well as the resulting mutant angiogenin proteins.

It has now been unexpectedly found that replacement of the lysine at or corresponding to position 40 (Lys.40) of human angiogenin with another amino acid, in particular, glutamine (Gln), or arginine (Arg). by site-specific mutagenesis of an angiogenin gene, results in mutant angiogenin proteins with significantly decreased angiogenic activity In addition, it has been found that replacement of the histidine at or corresponding to position 13 (His-13) or position 114 (His.114) of human angiogenin acid, in particular, alanine, by site-specific mutagenesis of an angiogenin gene, unexpectedly results in mutant angiogenin proteins with significantly decreased angiogenic activity. Such mutant angiogenin proteins with decreased angiogenic activity may be effective inhibitors of angiogenin-induced angiogenesis. In addition to decreased angiogenic activity, these mutant angiogenin proteins with replacements of the lysine at or corresponding to position 40 (Lys.40) or of the histidine at or corresponding to position 13 (His-13) or 114 (His-114) exhibit significantly decreased ribonucleolytic activity.

BACKGROUND ART

Angiogenesis, the process of developing a hemovascular network, is essential for the growth of solid tumors and is a component of normal wound healing and growth processes. It has also been implicated in the pathophysiology of atherogenesis, arthritis, and diabetic retinopathy. It is characterized by the directed growth of new capillaries toward a specific stimulus. This growth, mediated by the migration of endothelial cells, may proceed independently of endothelial cell mitosis.

The molecular messengers responsible for the process of angiogenesis have long been sought. Greenblatt and Shubik (J. Natl. Cancer Inst. 41: 111-124, 1968) concluded that tumor-induced neovascularization is mediated by a diffusible substance. Subsequently, a variety of soluble mediators have been implicated in the induction of neovascularization. These include prostaglandins (Auerbach, in *Lymphokines*, Pick and Landy, eds., 69-88, Academic Press, New York, 1981), human urokinase (Berman et al., Invest. Opthalm. Vis. Sci. 22:191-199, 1982), copper (Raju et al., J. Natl. Cancer Inst. 69: 1183-1188, 1982), and various "angiogenesis factors".

Angiogenesis factors have been derived from tumor cells, wound fluid (Banda et al., Proc. Natl. Acad. Sci USA 79:7773-7777, 1982; Banda et al., U.S. Pat. No. 4,503,038), and retinal cells (D'Amore, Proc. Natl. Acad. Sci. USA 78:3068-3072, 1981). Tumor-derived angiogenesis factors have in general been poorly characterized. Folkman et al. (J. Exp. Med. 133: 275-288, 1971) isolated a tumor angiogenesis factor from the Walker 256 rat ascites tumor. The factor was mitogenic for capillary endothelial cells and was inactivated by RNase. Tuan et al. (Biochemistry 12:3159-3165, 1973) found mitogenic and angiogenic activity in the nonhistone proteins of the Walker 256 tumor. The active fraction was a mixture of proteins and carbohydrate. A variety of animal and human tumors have been shown to produce angiogenesis factor(s) (Phillips and Camber, Int. J. Cancer 23: 82-88, 1979) but the chemical nature of the factor(s) was not determined. A low molecular weight non-protein component from Walker 256 tumors has also been shown to be angiogenic and mitogenic (Weiss et al., Br. J. Cancer 40: 493-496, 1979). An angiogenesis factor with a molecular weight of 400-800 daltons was purified to homogeneity by Fenselau et al. (J. Biol. Chem. 256: 9605-9611, 1981), but it was not further characterized. Human lung tumor cells have been shown to secrete an angiogenesis factor comprising a high molecular weight carrier and a low molecular weight, possibly non-protein, active component (Camber et al., Int. J. Cancer 32:461-464,1983). Vallee et al. (Experientia. 41:1-15, 1985) found angiogenic activity associated with three fractions from Walker 256 tumors. Tolbert et al. (U.S. Pat. No. 4,229,531) disclose the production of angiogenesis factor from the human adenocarcinoma cell line HT-29, but the material was only partially purified and was not chemically characterized. Isolation of genes responsible for the production of angiogenesis factors has not heretofore been reported at least in part due to the lack of purity and characterization of the factors.

Isolation of angiogenesis factors has employed high performance liquid chromatography (Banda et al., ibid); solvent extraction (Folkman et al., ibid); chromatography on silica gel (Fenselau et al., ibid), DEAE cellulose (Weiss et al., ibid), or Sephadex (Tuan et al., ibid); and affinity chromatography (Weiss et al., ibid).

Recently, Vallee et al. (U.S. Patent No. 4,727,137, which is hereby incorporated by reference) have purified an angiogenic protein from a human adenocarcinoma cell line. The protein has been identified in normal human plasma (Shapiro, et al. Biochem. 26:5141-5146, 1987). The purified protein, known as angiogenin, was chemically characterized and its amino acid sequence determined. Two distinct, although apparently linked, biological activities have been demonstrated for the human tumor-derived angiogenin. First, it was reported to behave as a very potent angiogenic factor in vivo (Fett et al., Biochem. 24:5480-5486, 1985). Second, it has been found to exhibit a characteristic ribonucleolytic activity (Shapiro et al., Biochem. 25:3527-3532, 1986).

Denefle et al. (Gene 56:61-70, 1987), have prepared a synthetic gene coding for human angiogenin. The gene was designed to use codons found in highly expressed *E. coli* proteins and was ligated into a pBR322-derived expression vector constructed to contain the *E. coli* tryptophan (trp) promoter. This *E. coli*-produced angiogenin was found to be insoluble but could be easily renatured and purified. The purified angiogenin exhibited angiogenic activity and ribonucleolytic activity similar to that described for natural angiogenin purified by Vallee et al. (U.S. Patent No. 4,727,137) from human adenocarcinoma cells.

Hoechst (German Patent Application P3716722.7) has prepared a different synthetic gene for angiogenin with a leucine at position 30. In addition, this synthetic gene was designed to use codons preferentially expressed in *E. coli*. The gene was subcloned into a vector containing a modified trp promoter (European Patent Application 0198415) and a translation initiation region (TIR) sequence (Gene 41:201–206, 1986; EMBO J. 4:519–526, 1985) to increase translation efficiency. The synthetic gene is under direct control of the trp promoter and expression is induced by addition of indole-3-acrylic acid or by tryptophan starvation. The leu-30 angiogenin protein could be purified and was found to exhibit angiogenic and ribonucleolytic activity similar to that of natural angiogenin.

All the angiogenic proteins just described, whether plasma-derived, tumor cell-derived or recombinant DNA-derived (genomic DNA or synthetic gene derived) exhibit both angiogenic activity and ribonucleolytic activity. These two activities have not yet been separated. Indeed, one of the most intriguing features of angiogenin is its structural homology with mammalian pancreatic ribonucleases (RNases). Overall, there is a 35% sequence identity between human pancreatic RNase and angiogenin (Strydom et al., Biochemistry 24:5486–5494, 1985). This structural relationship should permit the study of the mechanism of action of angiogenin, as well as the relationship between the angiogenic and enzymatic (riboncleolytic) activities of angiogenin.

Because angiogenesis factors play an important role in wound healing (Rettura et al., FASEB Abstract #4309, 61st Annual Meeting, Chicago, 1977) and may find applicability in the development of screening tests for malignancies (Klagsbrun et al., Cancer Res. 36:110–114, 1976; and Brem et al., Science 195:880–881, 1977), it is clearly advantageous to produce angiogenic proteins in sufficient quantities to permit their application in therapy and diagnosis. The techniques of genetic engineering are ideally suited to increase production levels of these proteins. The cloning of genes encoding angiogenic proteins is a necessary first step in such large-scale production. In addition to increasing production levels of angiogenic proteins, it would be highly advantageous to use cloned genes to produce a mutant or variant angiogenin proteins with angiogenic activity that is much increased or much decreased over wild-type activity. The techniques of site-specific mutagenesis and genetic engineering are ideally suited to producing proteins with such increased or decreased activity. Although it is clear that the amino acids of an angiogenic protein may be modified by such techniques to produce proteins with altered biological activities, it is difficult to predict which amino acids should be altered and whether such an alteration will increase or decrease biological activity.

Furthermore, it may in some instances be desirable to obtain these mutant angiogenin proteins with altered angiogenic activity from non-tumor cells, such as in the case of human therapeutics, where contamination with certain tumor products would be unacceptable. This invention therefore provides for the production of angiogenin proteins in non-tumor cells with decreased angiogenic activity using site-specific mutagenesis and recombinant DNA techniques.

DISCLOSURE OF THE INVENTION

It has now been unexpectedly found that replacement of lysine at or corresponding to position 40 of human angiogenin by another amino acid, specifically by Gln or Arg, using site-specific mutagenesis of an angiogenin gene, results in mutant proteins with significantly decreased angiogenic potency. In addition, it has been found that replacement of the histidine at or corresponding to position 13 (His-13) or position 114 (His.114) of human angiogenin with another amino acid, in particular, alanine, by site-specific mutagenesis of an angiogenin gene, unexpectedly results in a significant decrease in the angiogenic activity of the modified angiogenin. These replacements also result in significant decreases of the ribonucleolytic activity of the modified angiogenin.

Briefly stated, the present invention discloses mutant or variant DNA sequences encoding mutant angiogenin proteins having reduced angiogenic activity. A DNA sequence encoding a mutant angiogenin, or a mutant protein having substantially the same biological activity as angiogenin, but with lower activity than that of non-mutated or wild-type angiogenin, is also disclosed. The DNA sequences may be obtained by site-specific mutagenesis of a DNA sequence encoding angiogenin (wild-type DNA sequence). The wild-type sequence suitable for mutagenesis may be any DNA segment encoding angiogenin, and may be cDNA, genomic DNA or may be a synthetic gene. Thus, a mutant angiogenin protein may be produced which exhibits biological activity qualitatively similar to, yet quantitatively different from, the activity exhibited by wild-type angiogenin.

The invention further discloses vectors comprising a mutant or variant DNA sequence encoding a mutant or variant protein having reduced angiogenic activity. Vectors comprising a DNA sequence encoding a protein having substantially the same but decreased biological activity as non-mutant or wild-type angiogenin are also disclosed. The vectors further comprise a promoter sequence upstream of and operably linked to the DNA sequence. In general, the vectors will also contain a selectable marker, and, depending on the host cell used, may contain such elements as regulatory sequences, polyadenylation signals, enhancers, and RNA splice sites.

An additional aspect of the present invention discloses cells transfected or transformed to produce a mutant protein having reduced angiogenic activity. Cells transfected or transformed to produce a mutant or variant protein having substantially the same, but decreased biological activity as non-mutant or wild-type angiogenin are also disclosed. The cells are transfected or transformed to contain an expression vector comprising a DNA sequence encoding a mutant or variant protein having reduced angiogenic activity. While expression of the gene encoding for the Lys.40, His.13 and His 114 mutant angiogenin protein is illustrated in bacteria, expression in yeast and mammalian cells is performed by art-recognized techniques and is contemplated by this invention.

A further aspect of the present invention discloses a method for producing a mutant or variant protein having reduced angiogenic activity. The method comprises (a) obtaining a mutant or variant angiogenin gene by site-specific mutagenesis of a non-mutant or wild-type angiogenin gene; (b) introducing into a host cell a vector comprising a DNA sequence encoding a mutant or variant protein having angiogenic activity; (c) growing the host cell in an appropriate medium; and (d) isolating the mutant or variant protein product encoded by the DNA sequence and produced by the host cell. A method for producing a mutant or variant protein having substantially the same but substantially decreased biological activity as angiogenin is also disclosed. The mutant proteins produced by these methods are also disclosed. In addition, portions of the human angiogenin proteins having the lysine corresponding to Lys.40 or the histidine corresponding to His.13 or His.114 altered are likewise encompassed by the present invention.

Other aspects of the invention will become evident upon reference to the detailed description and drawings.

BRIEF DESCRIPTION OF THE DRAWINGS

FIG. 1 illustrates the amino acid sequence of angiogenin purified from human adenocarcinoma HT-29 cells.

FIG. 3 illustrates a portion of the sequence of the genomic DNA insert in λHAG1. The cDNA insert of pHAG1 corresponds to nucleotides 106 to 731 of the genomic DNA, with a substitution at nucleotide 252.

FIG. 7 illustrates the DNA sequence of a synthetic angiogenin gene and the amino acid sequence encoded by this gene.

BEST MODE FOR CARRYING OUT THE INVENTION

Figure 2:
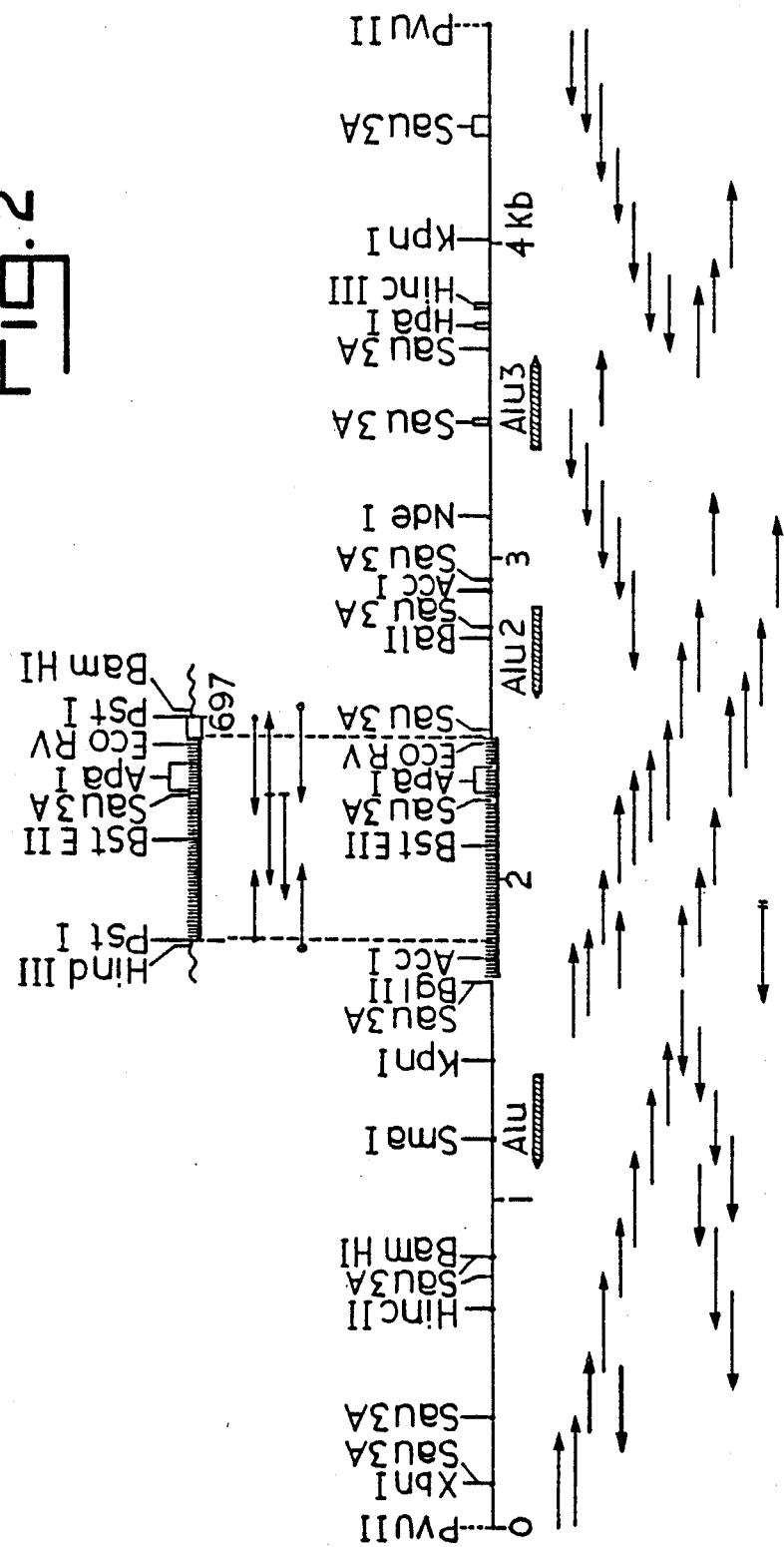
FIG. 2 illustrates the strategy used for sequencing the angiogenin cDNA and genomic clones. The top portion refers to the cDNA and the bottom portion to the genomic DNA. Solid bars indicate the coding regions, arrows indicate the fragments sequenced. The locations and directions of the three Alu sequences are indicated by large hatched arrows.

Prior to setting forth the invention, it may be helpful to define certain terms to be used hereinafter.

Biological activity, is a function or set of functions performed by a molecule in a biological context (i.e., in an organism or an in vitro facsimile). For angiogenin, biological activity is characterized by its angiogenic activity. It may also include ribonucleolytic activity.

Angiogenic activity, is the chemical stimulation of hemovascular development in tissue. It is generally associated with diffusible substances produced by a variety of cell types. Angiogenic activity may be characterized by a positive response in the chick embryo chorioallantoic membrane assay (Knighton et al., Br. J. Cancer 35:347-356, 1977) and/or the rabbit cornea implant assay (Langer and Folkman. Nature 263:797-800, 1976).

Ribonucleolytic activity is the ribonuclease (RNase) enzymatic activity associated with angiogenin, in particular, catalytic activity with certain RNA substrates, including the limited catalytic cleavage of rRNA and tRNA.

A mutant gene or a DNA construct is a DNA molecule, or a clone of such a molecule, which has been modified by human intervention to contain segments of DNA which are changed, combined or juxtaposed in a manner which would not otherwise exist in nature.

A mutant angiogenin protein is an angiogenin protein or any peptide fragment of that protein in which one or more amino acids have been replaced with other amino acids, and which has altered biological activity when compared with non-mutated or wild-type angiogenin.

Angiogenic proteins are produced by a variety of cell types, including tumor cells and retinal cells. Until recently, these proteins have not been obtained in sufficient purity to permit their chemical and physical characterization. Through the application of a novel multistep purification procedure, an exemplary angiogenic protein, hereinafter angiogenin, has been purified from culture media of a human tumor cell line. Determination of the protein sequence has allowed the isolation of corresponding DNA sequences and the expression of these sequences through recombinant DNA techniques.

The isolation of angiogenic proteins is based on the fractionation of conditioned cell media by ion exchange chromatography, followed by high performance liquid chromatography.

Although tumor cells are the preferred source of an angiogenic protein according to the present invention, other types of cells, notably retinal cells, are known to produce angiogenesis factors. A particularly preferred cell line is the human adenocarcinoma cell line HT-29 (Fogh and Trempe, in Human Tumor Cells in Vitro, Fogh, ed., 115-160, Plenum, N.Y., 1975). HT-29 isolates have been deposited with American Type Culture Collection under accession numbers HTB38 and CRL8905. The cells may be cultured according to known methods, e.g. as monolayer cultures in Dulbecco's modified Eagle's medium or other suitable media. A preferred medium is Dulbecco's modified Eagle's medium supplemented with 2 mM L-glutamine and 5% heat inactivated fetal bovine serum (DME/5). The medium is changed periodically and cells are subcultured according to known procedures.

To facilitate isolation of angiogenic protein(s) from the cell medium, it is preferred that the cells be transferred to a serum free maintenance medium once they have reached confluent growth. A preferred maintenance medium is DME/5 without serum but containing L-glutamine at a concentration of 5 mM.

Medium in which cells have been cultured or maintained, known as conditioned medium, is then removed from the cells and preferably filtered to remove cell debris, then treated to remove high molecular weight proteins. A preferred method of treatment is acidification, e.g. by the addition of glacial acetic acid to a concentration of 5% (v/v), followed by centrifugation. It may also be desirable to concentrate the filtered, acidified medium prior to further purification steps.

The filtered, treated medium is then chromatographed on a cation exchange matrix such as carboxymethyl cellulose (CM cellulose). It is preferred that the treated, conditioned medium be lyophilized, reconstituted in 0.1 M sodium phosphate buffer pH 6.6, and applied to the matrix. Under such conditions, the angiogenesis factor(s) will bind to the matrix and may be eluted with the same buffer containing 1 M NaCl.

The eluate from the cation exchange matrix is further fractionated by reversed-phase high performance liquid chromatography. The eluate is lyophilized, reconstituted in a suitable solvent, such as 0.1% trifluoroacetic acid (TFA) in water, and eluted by applying a gradient of a second solvent to the column. A linear gradient of isopropanol/acetonitrile/water (5:5:4 v/v/v) containing 0.08% TFA is preferred. Material eluted from the HPLC column may then be dialyzed to remove the solvent, lyophilized, and reconstituted.

The reconstituted HPLC column eluate is then assayed for angiogenic activity to identify the active fraction(s). Several assays for angiogenic activity are well known in the art, including the chick embryo chorioallantoic membrane assay (Knighton et al., Br. J. Cancer 35:347-356, 1977) and the cornea implant assay (Langer and Folkman, Nature 263:797-800, 1976).

When HT-29 cells are employed as the starting material, two active fractions are obtained from the HPLC column. One fraction contains a major protein component of $M_r \sim 16,000$ and lesser amounts of a $M_r \sim 14.000$ species. The second fraction contains a single protein species of $M_r \sim 14,000$, which has been designated angiogenin. On further analysis, angiogenin was found to have an isoelectric point greater than 9.5 and a molecular weight of approximately 14,193 daltons by amino acid sequence analysis. Surprisingly, in contrast to most previously described angiogenesis factors, angiogenin is not mitogenic in conventional assays. The amino acid sequence of angiogenin was found to be 35% homologous to the pancreatic ribonucleases.

When an angiogenic protein has been obtained in substantially pure form, its amino acid sequence is determined by known methods, for example, Edman degradation (Edman and Begg, Eur. J. Biochem. 1:80-91, 1967). It is not necessary to determine the entire amino acid sequence. Preferably, a sequence of at least 5-10 amino acids will be determined.

From the amino acid sequence, a DNA probe is designed. Generally, it will be necessary to design a family of probes corresponding to all of the possible DNA sequences encoding the amino acid sequence. It is preferred that such a probe be at least 14 nucleotides in length in order to minimize false positive signals when screening DNA clones. Suitable probes may be synthesized by known methods (for review, see Itakura, in *Trends in Biochemical Science*, Elsevier Biochemical Press, 1982) or purchased from commercial suppliers.

cDNA (complementary DNA) and/or genomic DNA libraries are then prepared and screened with the probe(s) using conventional hybridization techniques. Techniques for preparing such libraries are well known in the art (see, for example, Lawn et al., Cell 15:1157-1174, 1978; and Michelson et al., Proc. Natl. Acad. Sci. USA 80:472-476, 1983). Clones which hybridize to the probe(s) are then selected and sequenced.

Alternatively, if a sufficient quantity of pure angiogenic protein is obtained, it may be used to prepare an antibody, and the antibody in turn used to screen an expression cDNA library (Young and Davis. Proc. Natl. Acad. Sci. USA 80:1194-1198, 1983).

If a full length cDNA clone is obtained, it may be inserted directly into an expression vector for use in producing the angiogenic protein. Lacking a full length cDNA clone, the remaining coding sequence may be obtained by several methods, and a full length coding sequence may then be constructed. A cDNA clone may be used as a probe to screen additional cDNA libraries or to screen genomic DNA libraries. If the amino acid sequence of the protein is known, the missing material may be synthesized and joined to the cDNA and/or genomic DNA fragments to construct a complete coding sequence. Under some circumstances, it is preferred that the coding sequence further encode a leader peptide in order to facilitate proper processing and secretion of the angiogenic protein produced according to the present invention. The leader peptide may be that of the angiogenic peptide itself, or a heterologous leader peptide which functions in the particular host cell.

When a full length DNA sequence encoding an angiogenic protein has been obtained, it is then inserted into a suitable expression vector. Expression vectors for use in carrying out the present invention will further comprise a promoter operably linked to the DNA sequence encoding the angiogenic protein. In some instances it is preferred that expression vectors further comprise an origin of replication, as well as sequences which regulate and/or enhance expression levels, depending on the host cell selected. Suitable expression vectors may be derived from plasmids or viruses, or may contain elements of both.

Preferred prokaryotic hosts for use in carrying out the present invention are strains of the bacteria *Escherichia coli*, although Bacillus and other genera are also useful. Techniques for transforming these hosts and expressing foreign genes cloned in them are well known in the art (see, for example, Maniatis et al., *Molecular Cloning: A Laboratory Manual*, Cold Spring Harbor Laboratory, 1982). Vectors used for expressing foreign genes in bacterial hosts will generally contain a selectable marker, such as a gene for antibiotic resistance, and a promoter which functions in the host cell. Appropriate promoters include the trp (Nichols and Yanofsky, Meth. in Enzymology 101 155, 1983) lac (Casadaban et al., J. Bact. 143:971-980, 1980) and phage λ promoter systems. Plasmids useful for transforming bacteria include pBR322 (Bolivar, et al., Gene 2:95-113, 1977), the pUC plasmids (Messing, Meth. in Enzymology 101:20-77, 1983; and Vieira and Messing, Gene 19:259-268, 1982), pCQV2 (Queen, J. Mol. Appl. Genet. 2:1-10, 1983), and derivatives thereof.

Eukaryotic microorganisms, such as the yeast *Saccharomyces cerevisiae*, may also be used as host cells. Techniques for transforming yeast are described by Beggs (Nature 275:104-108, 1978). Expression vectors for use in yeast include YRp7 (Struhl et al., Proc. Natl. Acad. Sci. USA 76:1035-1039, 1979), YEp13 (Broach et al., Gene 8:121-133, 1979), pJDB248 and pJDB219 (Beggs, ibid), and derivatives thereof. Such vectors will generally comprise a selectable marker, such as the nutritional marker TRP, which allows selection in a host strain carrying a trp1 mutation. Preferred promoters for use in yeast expression vectors include promoters from yeast glycolytic genes (Hitzeman et al., J. Biol. Chem. 255:12073-12080, 1980; Alber and Kawasaki, J. Mol. Appl. Genet. 1:419-434, 1982) or alcohol dehydrogenase genes (Young et al., in *Genetic Engineering of Microorganisms for Chemicals*, Hollaender et al., eds., p.335, Plenum, N.Y., 1982; and Ammerer, Meth. in Enzymology 101:192-201, 1983). To facilitate purification of an angiogenic protein produced in a yeast transformant and obtain proper disulphide bond formation, a signal sequence, preferably from a yeast gene encoding a secreted protein, may be joined to the coding sequence for the angiogenic protein. A particularly preferred signal sequence is the pre-pro region of the MFα1 gene (Kurjan and Herskowitz, Cell 30:933-943, 1982).

Higher eukaryotic cells may also serve as host cells in carrying out the present invention. Cultured mammalian cells are preferred. Expression vectors for use in mammalian cells will comprise a promoter capable of directing the transcription of a foreign gene introduced into a mammalian cell. A particularly preferred promoter is the mouse metallothionein.1 (MT.1) promoter (Palmiter et al., Science 222:809-814, 1983). Also contained in the expression vectors is a polyadenylation signal, located downstream of the insertion site. The polyadenylation signal may be that of the cloned angiogenic protein gene, or may be derived from a heterologous gene.

Cloned gene sequences may then be introduced into cultured mammalian cells by, for example, calcium phosphate-mediated transfection (Wigler et al., Cell 14:725, 1978; Coraro and Pearson, Somatic Cell Genetics 7:603, 1981; Graham and Van der Eb, Virology 52:456, 1973). A precipitate is formed of the DNA and calcium phosphate, and this precipitate is applied to the cells. Some of the cells take up the DNA and maintain it inside the cell for several days. A small fraction of these cells (typically $10^{-4}$) integrate the DNA into the genome. In order to identify these integrants, a gene that confers a selectable phenotype (a selectable marker) is generally introduced into the cells along with the gene of interest. Preferred selectable markers include genes that confer resistance to drugs, such an neomycin, hygromycin, and methotrexate. Selectable markers may be introduced into the cell on a separate plasmid at the same time as the gene of interest, or they may be introduced on the same plasmid.

The copy number of the integrated gene sequence may be increased through amplification by using certain selectable markers (e.g., dihydrofolate reductase, which confers resistance to methotrexate). The selectable marker is introduced into the cells along with the gene of interest, and drug selection is applied. The drug concentration is then increased in a step-wise manner, with selection of resistant cells at each step. By selecting for increased copy number of cloned sequences, expression levels may be substantially increased.

Angiogenic proteins produced according to the present invention may be purified from the host cells or cell media by cation exchange chromatography and high performance liquid chromatography as described above.

It will be appreciated that other angiogenic proteins may be isolated by the above process. Different cell lines may be expected to produce angiogenic proteins having different physical properties. Additionally, variations may exist due to genetic polymorphisms or cell-mediated modifications of the proteins or their precursors. Furthermore, the amino acid sequence of an angiogenic protein may be modified by genetic techniques to produce proteins with altered biological activities. For example, based on the homology between angiogenin and ribonuclease, the cys residues at positions 26, 39, 57, 81, 92 and 107, the histidines at positions 13 and 114, and the lysine at position 40 are preferred sites for replacement by other amino acids by site-specific mutagenesis (Zoller et al., Manual for *Advanced Techniques in Molecular Cloning Course*, Cold Spring Harbor Laboratory, 1983). The resultant DNA sequence will encode a protein that will have substantially the same amino acid sequence as wild-type angiogenin, but exhibiting a higher or lower level of angiogenic activity. An increase in the biological activity could permit the use of lower dosage levels. A molecule having reduced angiogenic activity or no angiogenic activity, but retaining certain structural features, could still bind receptors on endothelial or other cells and, by blocking the site of action, form an antagonist to the action of the natural protein, resulting in an approach to the treatment of angiogenesis-related disease states. Such proteins are within the scope of the present invention.

Angiogenic proteins produced according to the present invention may be used to produce therapeutic or diagnostic compositions by combining them with suitable carriers. The therapeutic compositions may be used to promote the development of a hemovascular network in a mammal, for example, to induce collateral circulation following a heart attack, or to promote wound healing, for example in joints or other locations. Preferably, the therapeutic compositions according to the present invention will be administered intravenously or by direct topical application to the wound site. For example, if injury occurs to the meniscus of the knee or shoulder as frequently occurs in sports-related injuries or osteoarthritis, injection of angiogenic proteins at the site of the injury may promote healing of torn or traumatized fibrocartilage material. Effective doses will vary according to the severity of the condition and the target tissue. Furthermore, angiogenic proteins (wild-type or mutant) have diagnostic applications in screening for the presence of malignancies, either by using the protein to assay for the presence of antibodies or to produce antibodies for use as immunodiagnostic reagents. A diagnostic composition containing the protein may be incubated with a biological sample under conditions suitable for the formation of an antigen-antibody complex. The formation of the complex (i.e., the presence of antibodies in the sample) is then detected. Techniques for such assays are well known in the art, e.g. the enzyme linked immunosorbent assay (Voller et al., *The Enzyme Linked Immunosorbent Assay*, Dynatech Laboratories, Inc., 1979) or the Western blot assay (see, for example, Towbin et al., Proc. Natl Acad. Sci. USA 76:4350, 1979). Similarly, a diagnostic composition comprising an antibody against an angiogenic protein may be used to assay for the presence of the protein in a biological sample. The angiogenic proteins may also be used to develop angiogenesis inhibitors which may be useful in the treatment of disorders associated with angiogenesis.

Recombinant DNA provides a superior method for the production of these proteins in the quantities needed for these therapeutic applications.

EXPERIMENTAL

Materials and Methods

Restriction endonucleases, T4 DNA ligase, T4 kinase, alkaline phosphatase, endonuclease Bal 31 and Klenow fragment of DNA polymerase I coli) were purchased from Bethesda Research Laboratories or New England Biolabs. Reverse transcriptase (avian myeloma virus) was obtained from Seikagaku U.S.A., Inc. Dideoxynucleotide triphosphates, deoxynucleotide triphosphates, pBR322 and pUC13 were purchased from P-L Biochemicals. Universal primers (hepta decamer) for dideoxy sequencing were purchased from New England Biolabs, and the $[\alpha\text{-}^{32}P]dATP$, $[\gamma^{32}P]ATP$, and $[^{35}S]dATP\alpha S$ were obtained from Amersham.

EXAMPLE 1

Isolation of cDNA and Genomic Sequences Encoding Angiogenin.

A human cDNA library was prepared from human liver poly(A)-mRNA employing plasmid pUC13 as a cloning vector (Maniatis et al., ibid). This plasmid was previously tailed with G's at its PstI site according to the method of Michelson & Orkin, J. Biol. Chem., 257. 14773–14782 (1982). A mixture of 16 synthetic oligonucleotides [CCCTGAGGCTTAGC(A/G)TC(A/G)TA(A/G)TG(C/T)TG] was purchased from P.L Biochemicals and employed as a hybridization probe. The nucleotide mixture is complementary to nucleotide sequences that code for Gln-His-Tyr-Asp-Ala-Lys-Pro-Gln-Gly. This sequence is present in the amino-terminal region of human angiogenin isolated from the colon adenocarcinoma cell line HT-29 (see FIG. 1). The nucleotide mixture was radiolabeled with T4 kinase and [$^{32}$P]ATP to a specific activity of approximately 3 X $10^8$ cpm/μg and employed for the screening of 350,000 transformants from the liver library by the method of Wallace et al. (Nucleic Acids Res. 9:879–894, 1981). Seven recombinant plasmids that hybridized strongly with the probe were isolated and purified by cesium chloride gradient centrifugation. The DNA inserts in each of the positive clones were digested with various restriction enzymes and analyzed by polyacrylamide gel electrophoresis. Their sequence was determined by the chemical degradation method of Maxam & Gilbert (Meth. in Enzymology 65:499–560, 1980). Each sequence was determined two or more times, and greater than 85% of the sequence was determined on both strands.

The plasmid containing the largest cDNA insert (pHAG1) was then sequenced by the method of Maxam & Gilbert (ibid) according to the strategy shown in the top of FIG. 2. This cDNA insert contained 697 nucleotides and included 12 G's at the 5'end, a short noncoding sequence, a leader sequence coding for a signal peptide of 24 (or 22) amino acids, 369 nucleotides coding for the mature protein of 123 amino acids, a stop codon, 175 nucleotides of 3'noncoding sequence, a poly(A) tail of 36 nucleotides, and 23 C's on the 3'end. The cDNA insert corresponds to nucleotides 106 to 731 of the genomic DNA sequence shown in FIG. 3, with a substitution at nucleotide 252 (encoding a Gly at residue 23). Plasmid pHAG1 has been deposited with American Type Culture Collection under accession number 40192.

A human genomic library (Maniatis et al., Cell 15:687–702, 1978) consisting of about 3 X $10^6$ λCharon 4A bacteriophage was screened with the cDNA insert of clone pHAG1 which had been radiolabeled by nick translation (Rigby et al., J. Mol. Biol. 113:237–251, 1977). One strongly hybridizing phage clone, designated λHAG1, identified by the method of Benton & Davis (Science 196:181–182, 1977) was plaque purified, and the phage DNA was isolated by the plate lysis method (Maniatis et al., 1982, ibid). The genomic insert was analyzed by digestion with various restriction enzymes. A DNA fragment generated by digestion of the insert with PvuII was about 5 kilobases (kb) in size and strongly hybridized to the cDNA probe. This fragment was subcloned into plasmid pBR322 and subjected to DNA sequencing by the dideoxy method (Messing et al., Nucleic Acids Res. 9:309–321, 1981; Norrander et al., Gene 26:101–106, 1983) employing [$^{35}$S]dATPαS as described in the Amersham cloning and sequencing manual. A ~3 kb DNA fragment generated by digestion of the phage genomic insert with KpnI which strongly hybridized to the probe was subcloned into the M13mp18 phage vector and subjected to DNA sequencing employing the synthetic oligonucleotide probe as a primer. Systematic deletions of the genomic DNA with endonuclease Bal 31 were carried out essentially as described by Poncz et al. (Proc. Natl. Acad. Sci. USA 79:4298–4302, 1982), Guo & Wu (Meth. in Enzymology 100:60–96, 1983). About 95% of the genomic DNA sequence was determined two or more times, and greater than 50% of the genomic sequence was determined on both strands. A portion of this sequence corresponded to the coding sequence for angiogenin. The vector λHAG1 has been deposited with American Type Culture Collection under accession number 40193.

The gene for angiogenin was also found in a DNA fragment of about 5 kb that was generated by digestion of λHAG1 with PvuII. This DNA fragment was subcloned into pBR322 and subjected to DNA sequencing by the dideoxy chain termination method employing the strategy shown in the bottom of FIG. 2. The complete sequence of the gene for human angiogenin (FIG. 3) indicated that the gene contains about 800 nucleotides and is free of intervening sequences in the coding and 3'noncoding regions of the gene. The possibility of an intron(s) in the 5' flanking region cannot be excluded, however, since the largest cDNA did not extend into this region.

The gene for angiogenin contains three Alu repetitive sequences (Schmid & Jelinek, Science 216:1065–1070, 1982) in its flanking regions (FIGS. 2 and 3). The first Alu repeat was located in the immediate 5' flanking region of the gene, while the second was present in the immediate 3' flanking region. These two Alu repeats were in the same inverted orientation. The third Alu repeat was located about 500 nucleotides downstream from the second Alu sequence in the 3' flanking region of the gene and was in the typical orientation with the poly(A) on the 3' end of the 300 nucleotide sequence. Furthermore, each Alu repeat was flanked by a pair of short direct repeat sequences. The nucleotide sequences for the three Alu repeats were about 87% homologous to the consensus Alu sequence of Schmid & Jelinek (ibid).

A tentative TATA box (Goldberg, M.L., Doctoral Dissertation, Stanford University, 1979) and a transcription initiation site were identified at nucleotides −32 and +1 respectively, but no potential CAAT box was found in the immediate vicinity. A sequence of TCAAT was identified, however, at nucleotide −225 which is about 190 bp upstream from the proposed TATA box. Two sequences of AATAAA which are involved in the polyadenylation or processing of the messenger RNA at the 3'end (Proudfoot & Brownlee, Nature 263:211–214, 1976), were identified at nucleotides 703 and 707. Polyadenylation of the mRNA occurs at nucleotide 731 which is 20 nucleotides downstream from the end of the second AATAAA sequence. The consensus sequence of CACTG, which also may be involved in polyadenylation or cleavage of the mRNA at the 3'end (Berget, Nature 309:179–182, 1984), was present starting at nucleotide 747. A stretch of 32 nucleotides with alternating purine and pyrimidine was found starting with nucleotide 1416. This sequence provides a potential region for a left-handed helix structure or Z-DNA in the gene (Rich et al., Ann. Rev. Biochem. 53:791-846, 1984). A computer search of the flanking regions of the gene for angiogenin as well as in the complementary strand showed no open reading frames.

The amino acid sequence of human angiogenin is about 35% homologous with human ribonuclease. The location of the disulfide bonds in human angiogenin, as determined by direct protein sequence analysis, further emphasizes the homology to ribonuclease (Strydom et al., Biochemistry 24:5486-5494, 1985).

EXAMPLE 2

Production of Angiogenin in Transfected Mammalian Cells.

For expressing angiogenin in transfected mammalian cells, expression vector pHAGF-MT-DHFR, comprising the angiogenin genomic coding sequence (HAGF), the mouse metallothionein.1 (MT.1) promoter, and a DHFR selectable marker joined to the SV40 promoter, was constructed.

Figure 4:
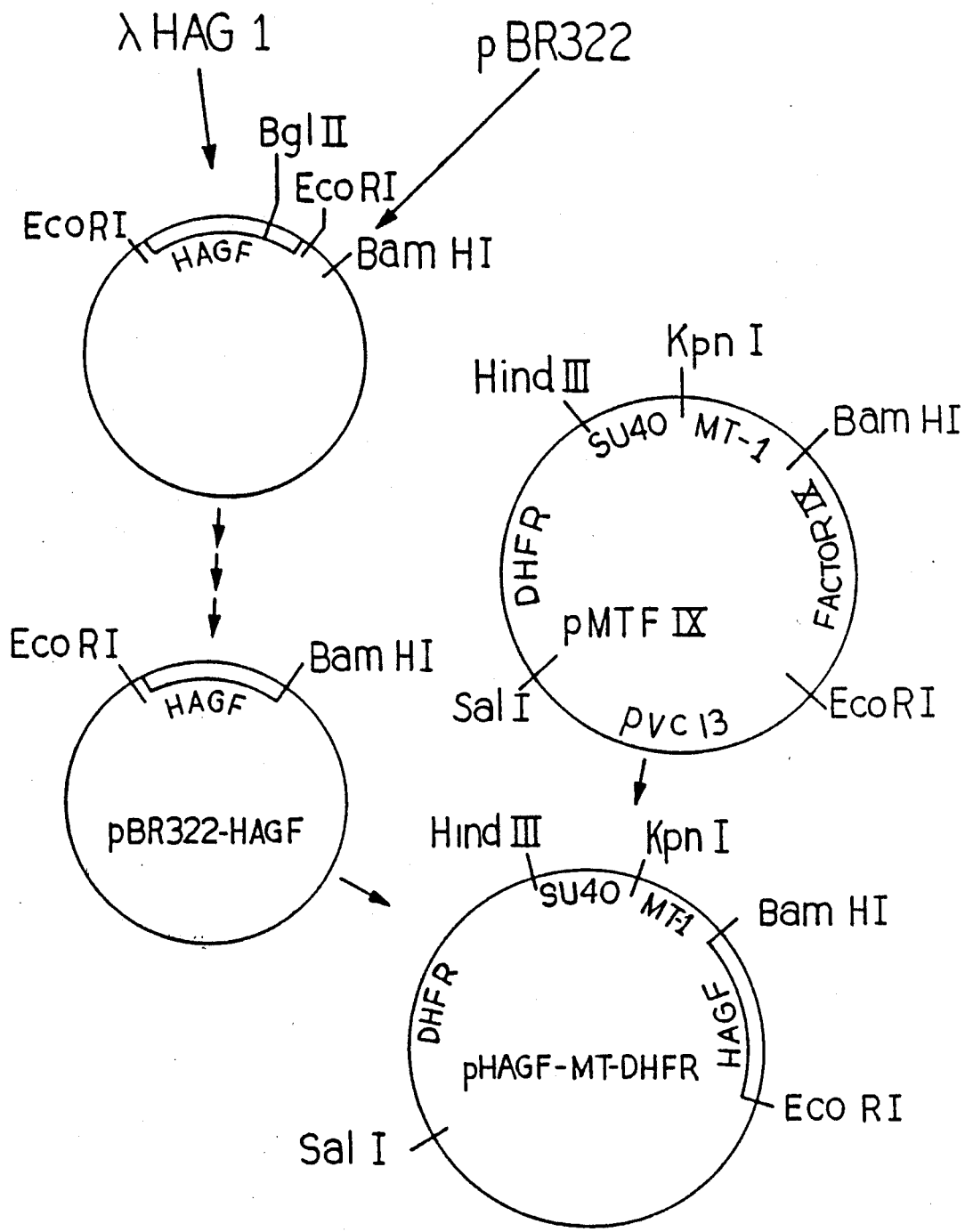
FIG. 4 illustrates the construction of the mammalian cell expression vector pHAGF-MT-DHFR.

As shown in FIG. 4, the HAGF insert was isolated from λHAG1 as a PvuII fragment and inserted into PBR322 which had been linearized with SmaI. The resultant plasmid was then digested with BglII, which cuts in the 5' untranslated region of the HAGF sequence. The DNA was then digested with Bal 31 to produce a HAGF sequence having a 5' terminus at nucleotide +7 from the site of transcription initiation. The DNA was then digested with BamHI. The resulting fragment ends were blunted using DNA polymerase I (Klenow fragment) and the fragment comprising the pBR322 and HAGF coding sequences was purified by electrophoresis on a 0.7% agarose gel. The DNA was extracted from the gel and recircularized. The resultant plasmid, designated pBR322-HAGF, was digested with BamHI and EcoRI and the ~3 kb fragment comprising the angiogenin sequence was purified by electrophoresis on a 0.7% agarose gel.

The final expression vector was then constructed in the following manner. Plasmid pMTFIX (Kurachi and Palmiter, Thrombosis and Hemostasis 54:282, 1985), comprising the mouse metallothionein (MT-1) promoter, human Factor IX coding sequence, SV40 promoter, and a modified DHFR gene (Levinson et al., EPO publication 117,060) was digested with BamHI and EcoRI (FIG. 4). The fragment comprising the pUC13 sequence and the SV40-DHFR expression unit was gel purified. This fragment was then joined to the BamHI-EcoRI HAGF fragment. The resultant vector was designated pHAGF-MT-DHFR (FIG. 4).

Plasmid pHAGF-MT-DHFR was then transferred into baby hamster kidney (BHK) cells by standard calcium phosphate-mediated transfection procedures. Cells containing the vector were grown at 37° C. in 5% C)2 in Dulbecco's modified Eagle's medium containing glucose and glutamine (Gibco), supplemented with 3.7 g/l NaHC03, 10% heat inactivated fetal calf serum and antibiotics. Cells containing the plasmid were then selected for methotrexate (MTX) resistance by sequentially increasing the concentration of MTX in the culture medium. MTX concentrations used were 1 μM, 10 μM, 100 μM, and 1 mM. Cells which survived in the presence of lmM MTX were then induced by the addition of either 80 μM ZnSO4, 2 μM CdSO4, or a mixture of the two salts to the culture medium.

Angiogenin mRNA was assayed essentially as described by Durnam and Palmiter (Analyt. Biochem. 131:385-393, 1983). Sense strand DNA from an M13mp18 clone containing the entire angiogenin gene in a ~2.9kb insert was used to make a standard curve. A 20-mer complementary to the coding sequence for amino acids 35 to 41 of angiogenin was labelled with $^{32}P$ at its 5'end and used as a probe in solution hybridization.

Messenger RNA levels were elevated >20-fold using $Cd^{++}$ induction and >15-fold for $Zn^{++}$ induction.

To assay for the presence of angiogenin, the induced, conditioned medium was acidified, frozen and thawed, centrifuged, and the supernatant dialyzed against water and lyophilized. The lyophilized material was then dissolved in and dialyzed against 0.1 M sodium phosphate buffer pH 6.6, supplemented with lysozyme as a carrier. The dialyzed sample was applied to a column of CM.52 cellulose and partially purified angiogenin was eluted with the same buffer containing 1 M NaCl. The eluate was applied to a C18 reversed phase HPLC column and fractionated as described above. A protein having the chromatographic and electrophoretic properties of tumor-derived angiogenin was obtained.

The resultant protein is assayed for angiogenic activity by the CAM method using published procedures.

EXAMPLE 3

Production of Angiogenin in Yeast.

Figure 6:
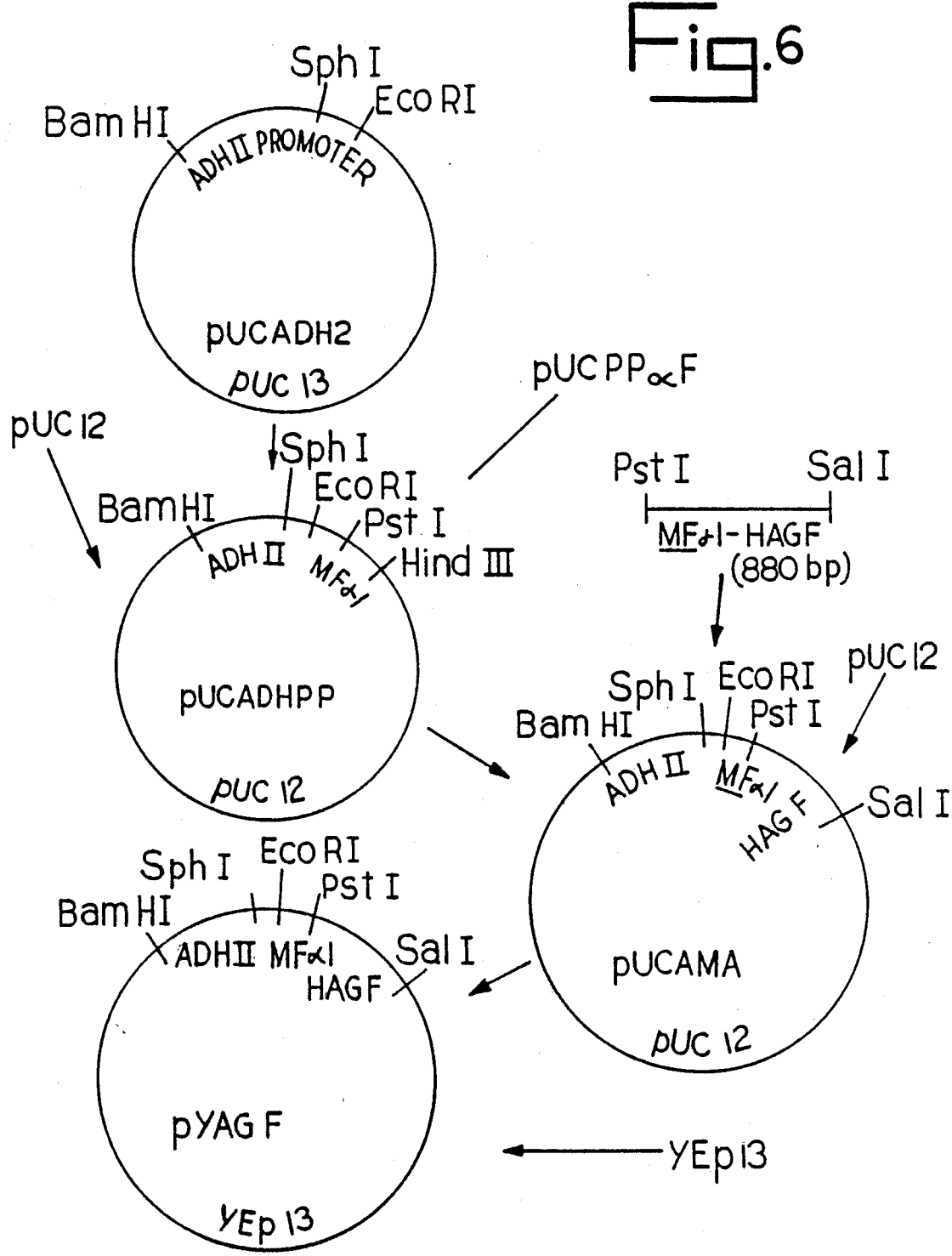

A vector for expressing angiogenin in transformed yeast is illustrated in FIG. 6. It contains an expression unit consisting of the yeast ADHII promoter (Young et al., in *Genetic Engineering of Microorganisms for Chemicals*, Hollaender et al., eds., p. 335, Plenum, N.Y., 1982), a portion of the MFα1 pre-pro sequence (Kurjan and Herskowitz, Cell 30:933.943, 1982), and the HAGF sequence.

A portion of the ADHII gene is obtained from the plasmid pADR2 (Beier and Young, Nature 300:724-728, 1982) as a SohI fragment of approximately 1530 bp. This fragment is subcloned into an M13 phage vector and mutagenized essentially as described by Zoller et al., *Manual for Advanced Techniques in Molecular Cloning Course*, Cold Spring Harbor Laboratory. 1983, using a mutagenic primer having the sequence GTA ATA CAC AGA ATT CAT TCC AGA AA. The replicative form of the mutagenized phage is digested with SohI and EcoRI and a partial ADHII promoter fragment of approximately 176 bp is purified. The upstream portion of the promoter is then restored by joining the ~176bp fragment, the ~1 kb BamHI-SphI fragment of ADHII (from pADR2), and BamHI +EcoRI cut pUC13. The resultant plasmid is designated pUCADH2 (FIG. 6).

Figure 5:
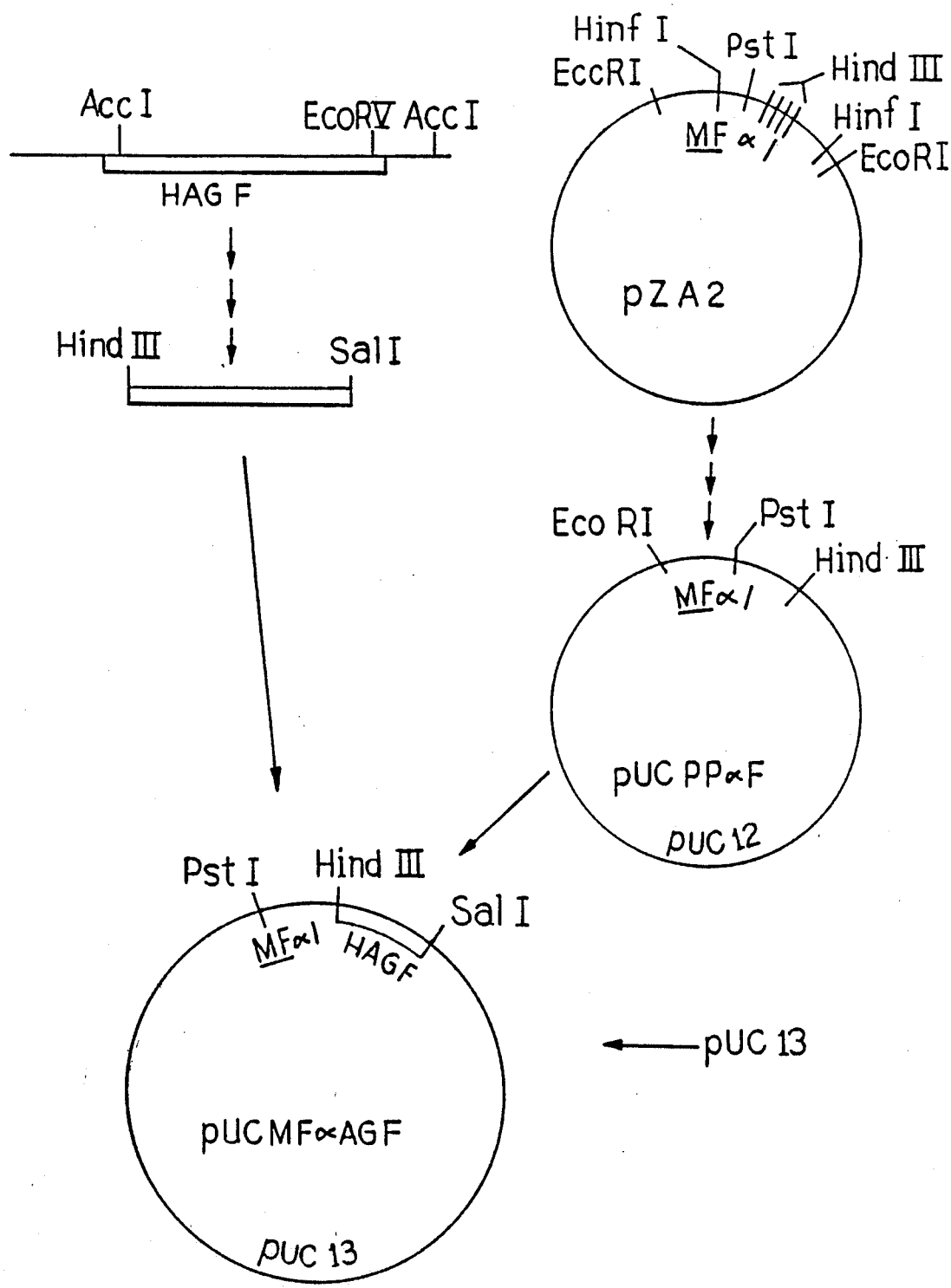
FIGS. 5 and 6 illustrate the construction of the yeast expression vector pYAGF.

Referring to FIG. 5, the MFα1 gene is obtained from a yeast genomic library of partial Sau3A fragments cloned into the BamHI site of YEp13 (Nasmyth and Tatchell, Cell 19:753-764, 1980) and identified by complementation of the matα2 mutation. One such clone is designated pZA2. The MFα1 sequence is cut at position −71 with HinfI, the ends filled using DNA polymerase I (Klenow fragment), and EcoRI linkers are added. The signal sequence is then isolated as an EcoRI-HindIII fragment and subcloned in pUC12 to construct plasmid pUCPPαF.

The HAGF coding sequence is isolated from λHAG1 as a 1115 bp AccI fragment. The fragment ends are blunted using DNA polymerase I (Klenow fragment) and HindIII linkers are added to the ends. The resultant fragment is digested with HindIII and EcoRV and a ~666 bp fragment is gel purified. SalI linkers are then ligated to the EcoRV terminus, the fragment is cut with SalI, and the ~674 bp fragment is gel purified.

The HAGF sequence is then joined to a portion of the MFα1 signal sequence. Plasmid pUCPPαF is digested with PstI and HindIII and the 237 bp fragment is isolated. The ~674 bp HAGF fragment and the 237bp MFα1 fragment are ligated to PstI +SalI cut pUC13. The resultant recombinant plasmid is digested with PstI and SalI and the ~911 bp MFα1-HAGF fragment is gel purified and inserted into PstI +SalI cut M13mp10 (replicative form). A precise junction between the Lys-Arg processing site of MFα1 and the first amino acid of angiogenin is achieved through in vitro mutagenesis of the resultant recombinant phage using the mutagenic primer TGG ATA AAA GAC AGG ATA ACTC. The replicative form of the mutagenized phage is cut with PstI and SalI and the ~880 bp MFα1 HAGF fragment is gel purified.

Referring to FIG. 6, the ADHII-MFα1-HAGF expression unit is then assembled. Plasmid pUCADH2 is cut with BamHI and EcoRI and the -1200 bp ADHII fragment is gel purified. Plasmid PUCPPαF is cut with EcoRI and HindIII and the -340 bp MFα1 fragment is gel purified. The two fragments are ligated to BamHI +HindIII cut pUC12 to construct pUCADHPP. This plasmid is digested with BamHI and PstI and the ~1300 bp ADHII MFα1 fragment is purified. This fragment and the ~880 bp MFα1 HAGF fragment are then joined, in a triple ligation, to BamHI +SalI cut pUC12. The resultant plasmid is designated pUCAMA.

The yeast expression vector pYAGF is constructed by ligating the BamHI-HindIII expression unit fragment from pUCAMA to BamHI+HindIII digested YEp13.

Yeast cells are transformed with pYAGF and cultured by conventional methods. Angiogenin is purified from cell extracts or culture media essentially as described above.

EXAMPLE 4

Preparation of *E. coli* Expression System for Recombinant Angiogenin

1. Construction of Synthetic Leu.30 Angiogenin Gene.

A gene coding for Leu.30 angiogenin was assembled from 12 chemically synthesized oligonucleotides as shown in FIG. 7. Oligonucleotide sequences were chosen so that they conformed largely to preferred codon usage in *E. coli* (Maruyama et al., Nucl. Acids Res. 14 Supplement:r151-197, 1986) and also contained restriction endonuclease cleavage sites that would facilitate mutagenesis. Complementary oligonucleotides designated a and b (FIG. 7) were annealed and then the following pairs were ligated using T4 ligase under standard conditions: 1ab with 2ab, 3ab with 4ab, and 5ab with 6ab. The resulting duplexes were ligated as shown in FIG. 7.

2. Construction of Angiogenin Expression Plasmids.

a. Expression Plasmid for Met.(.1)Leu.30 Angiogenin: pAng1

A pUC-derived cloning vector containing the *E. coli* trp promoter, an rrn$^B$ transcription termination sequence, a unique NcoI cleavage site at the initiation codon, and an ampicillinase marker for selection was provided by Dr. M. Leineweber (Hoechst A.G.). This vector was modified in the region 3' of the trp promoter in order to introduce sequences which increase translational efficiency in *E. coli* (McCarthy et al., EMBO J. 4:519-526, 1985; McCarthy et al., Gene 41:201-206, 1986). The modification was achieved by replacing the sequence located between the HpaI cleavage site in the promoter and the NcoI cleavage site with the following synthetic duplex:

```
         HpaI                                         KpnI
    AAC TAG TAC GCA AGT TCA CGT AAA AAG GTA CCT AAT TTA CCA
    TTG ATC ATG CGT TCA AGT GCA TTT TTC CAT GGA TTA AAT GGT

NcoI
    ACA CTA CTA CGT TTT AAC TGA AAC AAA CTG GAG ACT GC
    TGT GAT GAT GCA AAA TTG ACT TTG TTT GAC CTC TGA CGG TAC
```

In this modification the sequence preceding the KpnI recognition site is the same as in the original promoter, the KpnI site replaces the original Shine-Dalgarno sequence and the sequence between the KpnI site and the initiation codon is identical to that described by McCarthy et al., Gene 41:201-206, 1986. This modification resulted in an ~3.fold increase in angiogenin production as assessed by SDS-PAGE analysis. In order to obtain the angiogenin expression plasmid PAng1, this vector was cleaved with NcoI and EcoRI, and ligated with the XhoI/EcoRI fragment of the synthetic gene coding for Leu.30 angiogenin described above (FIG. 7) and with an adapter containing NcoI and XhoI overhangs of the following sequence:

```
       NcoI                  XhoI
     C ATG CAG GAC AAC
         GTC CTG TTG AGC T
       Met Gln Asp Asn Ser Arg
```

The final plasmid cannot be cleaved by NcoI.

b. Expression Plasmid for Met-(−1) Met−30 Angiogenin: pAng2

Figure 8:
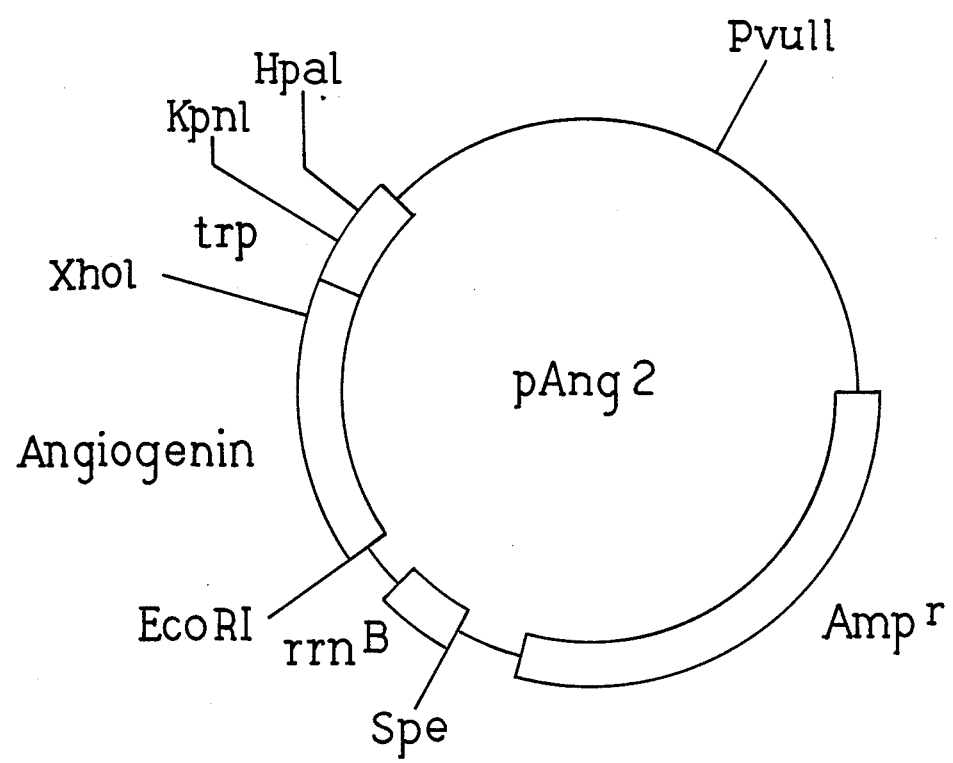
FIG. 8 illustrates the structure of plasmid expression vector pAng2.

The Met.(.1)Leu.30 angiogenin gene was removed from pAng1 by digestion with KpnI and EcoRI and inserted into M13mp18 by conventional methods. The leucine residue at position 30 was converted back to methionine as found in native angiogenin (FIG. 1) by oligonucleotide-directed mutagenesis by the method of Kunkel, Proc. Natl. Acad. Sci. USA 82:488-492, 1985, employing the Bio-Rad Muta-Gene ™ mutagenesis kit in combination with the mutagenic oligonucleotide PGAATCGATTATGAGACGCCG. Identification of plaques containing DNA sequences coding for Met.30 angiogenin was accomplished by chain termination DNA sequencing (Sanger et al., Proc. Natl. Acad. Sci. USA 74:5463-5467, 1977; Tabor and Richardson, Proc. Natl. Acad. Sci. USA 84:4767-4771, 1987) using a Sequenase ™ kit from United States Biochemicals. The coding region was sequenced in its entirety to ensure the absence of spurious mutations. The gene encoding Met-(−1)Met-30 angiogenin was excised from the double stranded M13 derivative using KonI and EcoRI, purified by electrophoresis in a 3% gel using NuSieve GTG low melting point agarose (FMC BioProducts), and ligated into gel purified expression vector containing KpnI/EcoRI ends. The final plasmid pAng2 is diagrammed in FIG. 8.

3. Bacterial Growth and Expression.

Expression plasmids pAng1 and pAng2 were propagated in *E. coli* strain W3110. Cultures were grown overnight at 37° C. in LB broth supplemented with ampicillin (50 μg/ml). In order to achieve optimal yields of angiogenin, these cultures were then diluted 100-fold into M9 medium (Maniatis et al., *Molecular Cloning, A Laboratory Manual*, pp. 68–69, Cold Spring Harbor Laboratory, 1982) supplemented with 0.4% casamino acids (Difco), 0.4% glucose, and 50 μg/ml ampicillin, and grown at 37° C. with vigorous shaking until the absorbance at 600nm reached 1.2 1.9 (-4 hours). Indole-3-acrylic acid (Aldrich) and glucose were then added to final concentrations of 10 or 20 μg/ml and 0.4%, respectively, and the cells were grown for an additional 4 to 5 hours.

4. Isolation of Met-(−1) Angiogenin and Removal of Met-(−1).

Cells grown as described above were collected by contrifugation at 4≠ C. for 10 minutes at 4000 g and resuspended in 1/10 of the original culture volume of ice-cold 20 mM Tris pH 7.6 containing 10% sucrose (Tris/sucrose buffer) and 2.5 mM phenylmethanesulfonyl-fluoride (PMSF). Lysozyme, NaC, and EDTA were then added to final concentrations of 100 μg/ml, 200 mM, and 10 mM, respectively, from 20- to 50-fold concentrated stocks and the mixture incubated for 45 minutes in an ice-water bath. Another 2.5 mM PMSF was then added and the mixture sonicated on ice for 7 cycles of 15 seconds each using a Branson Model 350 Sonifier, power setting 7 on "pulse" (70% on per second). Insoluble material was collected by centrifugation (17,300g, 25 minutes, 4° C.), the angiogenin-containing pellet washed with Tris/sucrose buffer containing 2.3 mM PMSF, and the pellet collected again by centrifugation. It was then resuspended in ice-cold water and the suspension centrifuged (34.800g, 30 minutes, 4° C.). The final pellet was resuspended in 7 M guanidine-HCl, 100 mM potassium phosphate pH 7.5 containing 100 mM 2.mercaptoethanol (Denefle et al., Gene 56:61–70 (1987) (10 ml/1 of original culture) and incubated for 3 hours at 37° C. The mixture was then added dropwise at 4° C. to 100 volumes of 50 mM Tris, pH 8.5, containing 100mM NaCl without stirring and allowed to stand for 20–24 hours. (Denefle et al., ibid) After stirring for 6.10 hours at 4° C., the NaCl concentration was increased to 1 M, and the mixture centrifuged for 30 minutes at 16, 300 g. The supernatant was then concentrated ~200.fold in an Amicon ultrafiltration device equipped with a YM 5 membrane. Six volumes of 10 mM Tris, pH 8.0, were then added and the mixture was reconcentrated, centrifuged (15,600 g, 15 minutes) and the supernatant chromatographed on a Mono S cation-exchange column as described by Shapiro et al., Biochemistry 26:5141–5146, (1987). This resulted in purification to near homogeneity, as judged by SDS-PAGE. Final purification, including removal of any endotoxin present, was accomplished by the C18 HPLC. Peak fractions from the Mono S column were applied to a Synchropak C18 HPLC column (Synchrom, Inc., 250 x 4.5 nm) and eluted with a 30 minute linear gradient of 30 to 50% solvent B at 0.8 ml/minute, where solvent A was 0.1% TFA in water and solvent B was 2-propanol:acetonitrile:water (3:2:2) containing 0.08% TFA. Peak fractions were dialyzed against water prior to testing for angiogenic and ribonucleolytic activity and for endotoxin content. Both the mobility on SDS-PAGE of the Met-(−1) angiogenin synthesized in *E. coli* and its elution time by C18 HPLC are identical to those of angiogenin synthesized by human cells. The amount of protein obtained was typically ~2 mg per liter of culture, representing a yield of 20–40%, based on estimates of angiogenin content in whole cell extracts by immunoblotting. In addition, the biological activity of the Met-(−1) angiogenin as measured by the chick chorioallantoic membrane (GAM) method (Knighton et al., Br. J. Cancer 35:347–356, 1977; Fett, et al., Biochemistry 24:5480–5486, 1985) was equivalent to that of angiogenin synthesized by human cells. Finally, the ribonucleolytic activity toward yeast tRNA of the Met-(−1) angiogenin as measured by the formation of perchloric acid-soluble fragments as described by Shapiro, et al., Proc. Natl. Acad. Sci. U.S.A. 84:8783–8787, 1987, was undistinguishable from that of angiogenin produced by human cells.

In order to remove the Met-(.1) from the angiogenin synthesized in *E. coli* and purified as just described, Met-(−1) angiogenin (7–10μM) was incubated with 1 nM *Aeromonas proteolytica* a aminopeptidase (Prescott and Wilkes, Meth. In Enzymology 45:530–543, 1976) in 200 mM potassium phosphate, pH 7.2, for 24 hours at 37° C. This material was then purified by chromatography on a Synchropak C18 HPLC column as described above. Amino acid analysis and Edman degradation experiments showed that the Aeromonas aminopeptidase had converted the *E. coli* produced Met-(−1) angiogenin to the naturally-occurring <Glu-1 form, by removal of the N-terminal methionine and subsequent cyclization of the new N-terminus to pyroglutamic acid.

EXAMPLE 5

Angiogenin Mutants

1. Preparation of Angiogenin Mutants.

Genes encoding angiogenin with a glutamine or arginine residue replacing Lys.40 or an alanine residue replacing His.13 or His.114 were obtained by the M13 oligonucleotide-directed mutagenesis method of Kunkel, Proc. Natl. Acad. Sci. U.S.A. 82:488–492 (1985) using the Bio-Rad Muta-Gene TM in vitro mutagenesis kit. The mutagenic oligonucleotides were pAGTCCGTGCCAAGATATCAAC (Gln.40). pGTCCGTGCAGAGATATCAAC (Arg.40), pCTGACCCAGGCCTATGACGC (His.13) and pTGCCAGTCGCTCTAGATCAG (His 114). Identification of plaques containing DNA sequences coding for the desired angiogenin mutants was accomplished by chain termination DNA sequencing (Sanger et al., Acad. Sci. U.S.A. 74:5463–5467, 1977; Tabor & Richardson, Proc. Natl. Acad. Sci. U.S.A. 84:4767–4771, 1987) using a Sequenase TM M kit from United States Biochemicals. The Lys.40 mutant angiogenin in which the Lys.40 was mutated to Gln.40 was designated K40Q. The Lys.40 mutant angiogenin in which the Lys.40 was mutated to Arg.40 was designated K40R. The mutant angiogenin in which His.13 was replaced by Ala-13 was designated H13A. The mutant angiogenin in which His-b 114 was replaced by Ala.114 was designated H114A.

An expression vector pAng2 containing a synthetic angiogenin gene, was prepared as described in Example 4. Plasmid pAng2 also contains a modified *E. coli* trp promoter, an rrn<sup>B</sup> transcription termination sequence, and an ampicillin resistance marker for selection. The genes for mutant angiogenins K40Q, K40R, H13A and H114A were transferred from M13mp18 into the expression vector pAng2. The DNA for each mutant was sequenced in its entirety in order to rule out any additional mutations. Mutant proteins were expressed in *E. coli* and purified to homogeneity as described in Example 4. There were no marked changes in chromatographic behavior during cation-exchange or C18 HPLC of the mutagenic derivatives compared with wild-type angiogenin. All preparations were at least 98% pure as judged by SDS-PAGE.

Plasmid pAng2.K40R in *E. coli* strain W3110 cells containing the K40R mutant angiogenin gene has been deposited with American Type Culture Collection under accession number A.T.C.C. 67749; plasmid pAng2-K40Q in *E. coli* strain W3110 cells containing the K40Q mutant angiogenin gene has been deposited with American Type Culture Collection under accession number A.T.C.C. 67751. Plasmid PAng2.H13A in *E. coli* strain W3110 cells containing the H13A mutant angiogenin gene has been deposited with American Type Culture Collec accession number A.T.C.C. 67833; plasmid pAng2.H114A in *E.coli* strain W3110 cells containing the H114A mutant angiogenin gene has been deposited with American Type Culture Collection under accession number A.T.C.C. 67834.

2. Structural Characterization of K40Q and K40R Angiogenin Mutants.

Amino acid compositions determined by the Picotag method (Waters Associates) of both K40Q and K40R mutant angiogenin (Table I) were in excellent agreement with that expected based on the primary structure of angiogenin and also consistent with the proposed mutations. As with the wild-type angiogenin, the presence of two methionines indicates that both proteins purified from the pAng2/*E. coli* expression system (see Example 4) contain a Met-(−1) residue. Tryptic peptide mapping was performed in order to determine the pairing of disulfide bonds and to ensure that no unexpected changes in primary structure had occurred. Tryptic peptides were obtained by digestions of the angiogenin mutants with HPLC purified trypsin according to the methods of Strydom et al., Biochemistry 24:5486–5494. These peptides were purified by reversed-phase HPLC on a Beckman Ultrasphere C18 column employing a linear gradient from 0% to 50% solvent B in 140 minutes, where solvent A is 0.1% TFA in water and solvent B is 3:2:2 mixture of 2.propanol: acetonitrile: water in 0.08% TFA.

The peptide maps of both mutant proteins were entirely consistent with the expected structures. In native angiogenin, residue 40 is contained in peptide T10, which elutes as a double peak as reported by Strydom et al., Biochemistry 24:5486–5494, 1985. With K40Q-angiogenin, peptides T8 and T10 are absent and a new peptide is observed which elutes immediately after T11. The composition of this peptide (Table II) indicates the presence of angiogenin sequence 83–95 and the modified sequence 34.51 expected for this mutation. Analyses of all other peptides were in good agreement with those of the wild-type protein. Compositions of these peptides demonstrate that all three disulfides have formed as in native angiogenin and the compositions account for all but four residues of the protein (Arg-32, Arg-33, Arg-122, and Pro-123).

TABLE I

Amino Acid Compositions of Angiogenin and Lys-40 Mutants Produced in *E. Coli*

| amino acid | angiogenin | K40Q | K40R |
|---|---|---|---|
| Asx | 15.3 (15)[1] | 15.3 | 15.3 |
| Glx | 10.0 (10) | 10.9 | 10.1 |
| Ser | 8.4 (9) | 8.5 | 8.0 |
| Gly | 8.0 (8) | 7.9 | 8.0 |
| His | 5.9 (6) | 6.0 | 5.8 |
| Arg | 13.0 (13) | 12.9 | 14.2 |
| Thr | 6.7 (7) | 6.7 | 6.8 |
| Ala | 5.1 (5) | 5.1 | 5.1 |
| Pro | 8.1 (8) | 8.1 | 8.0 |
| Tyr | 3.9 (4) | 4.0 | 3.8 |
| Val | 4.1 (5) | 4.1 | 4.5 |
| Met | 2.1 (2) | 2.2 | 2.0 |
| Ile | 6.5 (7) | 6.6 | 6.9 |
| Leu | 5.9 (6) | 5.8 | 6.1 |
| Phe | 4.9 (5) | 4.9 | 4.9 |
| Lys | 7.0 (7) | 6.0 | 5.7 |
| Cys | 5.7 (6) | 5.7 | 5.6 |

[1]In parentheses are the numbers of residues expected based on the amino acid sequence of angiogenin.

TABLE II

Amino Acid Compositions of Tryptic Peptides from Angiogenin Mutants

| amino acid | T8 + 10 K40Q | T 10 K40R |
|---|---|---|
| Asx | 3.81 (3)[1] | 0.26 |
| Glx | 2.59 (2) | 1.23 (1)[1] |
| Ser | 1.84 (2) | 1.95 (2) |
| Gly | 3.65 (4) | 3.25 (3) |
| His | 1.80 (2) | 1.00 (1) |
| Arg | 1.76 (2) | 2.03 (2) |
| Thr | 1.32 (2) | 1.04 (1) |
| Ala | 0.87 | 0.25 |
| Pro | 3.43 (4) | 3.73 (4) |
| Tyr | 0.70 (1) | 0.81 (1) |
| Val | 1.31 | |
| Met | | |
| Ile | 2.09 (2) | |
| Leu | 2.22 (2) | 2.04 (2) |
| Phe | 1.06 (1) | |
| Lys | 1.05 (1) | 0.29 |
| pmol analyzed | 24 | 60 |

[1]Numbers in parentheses represent compositions expected for disulfide-linked amino acids 34–51 + 83–95 (K40Q) or 34–40 + 83–95 (K40R). Values for some amino acids in the K40Q peptide are higher than expected due to contamination by peptide T11, which elutes immediately preceding it.

With the K40R mutant, the peptide map was essentially indistinguishable from that of the wild-type protein. The amino acid composition of peptide T10 (Table II) shows the replacement of a lysine by arginine and no other changes. The compositions of the remaining peptides were indistinguishable from those of unmodified angiogenin, and account for all of the molecule, except for Arg.32 and Arg.33. The compositions of peptides T9, 10, and 11 reveal that the disulfide bonds have formed correctly.

3. Structural Characterization of H13A and H114A Angiogenin Mutants.

Amino acid compositions determined by the Picotag method (Waters Associates) of both H13A and H114A mutant angiogenin (Table III) were in good agreement with that expected based on the primary structure of angiogenin and also consistent with the proposed mutations. As with the wild-type angiogenin, the presence of two methionines indicates that both proteins purified from the pAng2/*E. coli* expression system (see Example 4) contain a Met-(−1) residue. Tryptic peptide mapping was performed in order to determine the pairing of disulfide bonds and to ensure that no unexpected changes in primary structure had occurred. Tryptic peptides were obtained by digestions of the angiogenin mutants with HPLC purified trypsin according to the methods of Strydom et al., Biochemistry 24:5486–5494. These peptides were purified by reverse-phase HPLC on a Beckman Ultrasphere C18 column employing a linear gradient from 0% to 50% solvent B in 140 minutes, where solvent A is 0.1% TFA in water and solvent B is a 3:2:2 mixture of 2.propanol: acetonitrile: water containing 0.08% TFA.

TABLE III

Amino Acid Compositions of Angiogenin and His-13 and His-114 Produced in E. Coli

| amino acid | angiogenin | H13A | H114A |
|---|---|---|---|
| Asx | 14.8 (15)[1] | 15.0 | 14.6 |
| Glx | 10.0 (10) | 10.0 | 10.0 |
| Ser | 8.6 (9) | 8.1 | 8.5 |
| Gly | 8.0 (8) | 8.1 | 8.2 |
| His | 5.9 (6) | 4.9 | 4.9 |
| Arg | 13.0 (13) | 12.9 | 12.9 |
| Thr | 7.1 (7) | 7.1 | 7.0 |
| Ala | 5.1 (5) | 6.1 | 6.0 |
| Pro | 8.1 (8) | 8.0 | 8.3 |
| Tyr | 3.9 (4) | 3.9 | 3.9 |
| Val | 4.2 (5) | 4.2 | 4.2 |
| Met | 2.0 (2) | 2.0 | 2.0 |
| Ile | 6.7 (7) | 6.7 | 6.6 |
| Leu | 6.1 (6) | 6.0 | 6.1 |
| Phe | 5.0 (5) | 5.0 | 4.9 |
| Lys | 6.8 (7) | 6.8 | 7.2 |

[1]In parentheses are the numbers of residues expected based on the amino acid sequence of angiogenin.

The peptide maps of both mutant proteins were entirely consistent with the expected structures. In native angiogenin, the His-13 residue is contained in peptide T7. The map for the H13A mutant indicates that peptide T7 elutes somewhat later than peptide T7 from native angiogenin, as expected for a replacement of His with Ala. The amino acid composition of the peptide (Table IV) shows the replacement of His by Ala and no other changes. In native angiogenin, His-114 is contained in peptide T11. The map for the H114A mutant indicates that peptide T11 elutes later than peptide T11from native angiogenin, again as expected for a replacement of His with Ala. The amino acid composition of the peptide (Table IV) shows the replacement of His by Ala and no other changes.

TABLE IV

Amino Acid Compositions of Tryptic Peptides from Angiogenin Mutants

| amino acid | T7 H13A | T11 H114A |
|---|---|---|
| Asx | 0.93 (1) | 4.00 (4) |
| Glx | 1.86 (2) | 2.99 (3) |
| Ser |  | 1.03 (1) |
| Gly | 1.11 (1) | 1.17 (1) |
| His | 1.05 (1) |  |
| Arg | 0.89 (1) | 1.03 (1) |
| Thr | 1.93 (2) |  |
| Ala | 1.95 (2) | 2.89 (3) |
| Pro | 1.07 (1) | 1.19 (1) |
| Tyr | 1.80 (2) |  |
| Val |  | 2.95 (4) |
| Met |  |  |
| Ile |  | 1.70 (2) |
| Leu | 0.98 (1) | 2.03 (2) |
| Phe | 0.96 (1) | 0.82 (1) |
| Lys | 1.03 (1) | 0.82 (1) |

TABLE IV-continued

Amino Acid Compositions of Tryptic Peptides from Angiogenin Mutants

| amino acid | T7 H13A | T11 H114A |
|---|---|---|
| pmol analyzed | 175 | 90 |

Numbers in parentheses represent compositions expected for amino acids 6–21 (H13A) and the disulfide linked amino acids 55–60 + 102–121 (H114A). The composition of peptide T7 has been corrected for the presence of 0.22 equivalents of peptide T8 and 0.15 equivalents of peptide T9.

4. Circular Dichroic Spectra.

In order to examine whether the mutant angiogenins had undergone any extensive changes in secondary structure, circular dichroic spectra were measured from 205 to 300 nm. Spectra were recorded at 25° C. on a Cary 60 spectropolarimeter. Mutant and wild-type angiogenins were ~1.5 μM in 1 mM Tris, pH 8.0. Molar ellipticity was calculated as a function of wavelength from the observed spectrum corrected for the spectrum of the buffer alone in the identical optical cell. Spectra for wild-type, K40Q mutant angiogenin, and K40R mutant angiogenin were indistinguishable.

5. Enzymatic Activity of Angiogenin Mutants.

The ribonucleolytic activity of mutant angiogenins toward yeast tRNA (Type X. Sigma Chemical Co.) was determined by measuring formation of perchloric acid-soluble fragments as described by Shapiro et al.. Proc. Natl. Acad. Sci. U.S.A. 84:8783–8787, (1987). For K40Q and the K40R angiogenins the reaction times were 4 hours and 5 hours, respectively, and enzyme concentrations of 10.6 μM (K40Q) and up to 4.6 μM (K40R) were employed. The K40Q mutant was essentially inactive, allowing an upper limit to be set at 0.05% activity compared with the wild-type enzyme. The K40R mutant, in contrast, was 2.2% as active as the wild-type. For the H13A and H114A angiogenin mutants the reaction times were 4 hours and enzyme concentrations of up to 10.4 μM (HI14A) and 5.2 μM (HI14A) were employed. Both mutants had <0.02% activity (the detection limit of the assay employed) compared with the wild-type enzyme.

6. Biological Activity or Angiogenin Mutants.

The angiogenic activity of the K40Q, K40R, H13A and H114A mutants was assayed at the 1, 5, and 10 ng levels using the chick chorioallantoic membrane (CAM) method (Knighton et al., Br. J. Cancer 35:347–365, 1977; Fett et al., Biochemistry 24:5480–5486, 1985). The number of eggs employed in any individual set of assays at a given concentration ranged from 6 to 14. These assays revealed that the mutant proteins had substantially reduced activity as shown in Tables V, VI and VII. Even at 10 ng/egg, the percentage of positive responses was considerably lower than observed with the wild-type protein at 1 ng/egg.

TABLE V

Angiogenic Activity of Wild-type and K40Q Angiogenins[1]

| sample | dose (ng) | % positives (total number of eggs) |
|---|---|---|
| wild-type | 10 | 60 (62) |
| angiogenin | 5 | 58 (69) |
|  | 1 | 49 (61) |
| K40Q- | 10 | 27 (64) |
| angiogenin | 5 | 27 (66) |

TABLE V-continued

Angiogenic Activity of Wild-type and K40Q Angiogenins[1]

| sample | dose (ng) | % positives (total number of eggs) |
|---|---|---|
| | 1 | 21 (53) |

[1]Data obtained with two different preparations of both wild-type angiogenin and K40Q angiogenin did not differ significantly and were combined. Control samples containing only water assayed simultaneously were 18% positive (total of 56 eggs).

TABLE VI

Angiogenic Activity of Wild-type and K40R Angiogenins[2]

| sample | dose (ng) | % positives (total number of eggs) |
|---|---|---|
| wild-type angiogenin | 10 | 36 (14) |
| | 5 | 36 (11) |
| | 1 | 36 (11) |
| K40R angiogenin | 10 | 17 (12) |
| | 5 | 8 (12) |
| | 1 | 13 (15) |

[2]Control samples containing only water assayed simultaneously were 0% positive (total of 9 eggs).

TABLE VII

Angiogenic Activity of Wild-type and H13A-, and H114A-angiogenins[3]

| sample | dose (ng) | % positives (total number of eggs) |
|---|---|---|
| wild-type angiogenin | 10 | 58 (19) |
| | 5 | 47 (19) |
| | 1 | 47 (17) |
| H13A-angiogenin | 10 | 22 (18) |
| | 5 | 18 (17) |
| | 1 | 26 (19) |
| H114A-angiogenin | 10 | 25 (20) |
| | 5 | 29 (17) |
| | 1 | 19 (16) |

[3]These data are all from a single group of CAM assays. The water control sample assayed simultaneously gave 18% positives (1 out of 12).

7. Inhibition of Angiogenin-Induced Angiogenesis by Mutant Angiogenin

The capacity of the H13A mutant angiogenin to inhibit angiogenesis was examined using the chick chorioallantoic membrane method (Table VIII.). Implantation of 1 ng of wild-type angiogenin induced positive responses on 50% of the eggs. Addition of 20 ng of the H13A mutant to 1 ng of the wild-type angiogenin decreased the positive responses to 27%, essentially the same as observed with 20 ng of the H13A mutant by itself. Thus, the mutant angiogenin appears to prevent the induction of angiogenesis by wild-type angiogenin.

TABLE VIII

Inhibition of Angiogenesis by Mutant Angiogenin

| sample | dose (ng) | % positives (total # of eggs) |
|---|---|---|
| wild-type angiogenin | 1 | 49 (43) |
| H13A-angiogenin | 20 | 20 (44) |
| wild-type + H13A-angiogenin | 1 + 20 | 27 (41) |
| wild-type + H13A-angiogenin | 1 + 5 | 19 (15) |
| wild-type + H13A-angiogenin | 1 + 1 | 40 (15) |

Control samples containing only water assayed simultaneously were 15% positive (total of 27 eggs).

EXAMPLE 6

Interaction of Mutant Angiogenin With Human Placental Ribonuclease Inhibitor

1. Rate of Association.

Angiogenin binds extremely tightly tot he human placental RNase inhibitor (PRI) [$K_i$_7 X 10$^{-16}$], a 51,000 dalton cytoplasmic protein originally studied as an inhibitor of RNase A (Blackburn, J. Biol. Chem. 254:12484–12487, 1977). Both the angiogenic and ribonucleolytic activities of angiogenin have been shown by Shapiro and Vallee, Proc. Natl. Acad. USA 84:2238–2241, 1987, to be abolished upon formation of the complex of angiogenin with PRI.

The effect of substitution at position 40 of Lys to Arg or Gln on the binding to PRI was determined by using the K40R and K40Q mutant angiogenins, respectively. Human placental ribonuclease inhibitor (PRI) was isolated by the method of Blackburn, J. Biol. Chem., 254:12484–12487, 1979. Concentrations of PRI solutions were determined by inhibition of RNase A activity toward cytidylyl-(3' -5') guanosine CpG using a four point titration plot. Such a plot is linear under the conditions employed, i.e. [PRI]>>$K_i$. The apparent second-order rate constants of association for PRI with wild-type, K40R and K40Q angiogenins were determined by examining their competition with RNase A for PRI (Shapiro & Vallee, Proc. Natl. Acad. Sci. USA 84:2238–2241, 1987.)

Bovine pancreatic RNase A was purchased from Cooper Biomedical and was quantitated using molar absorptivity at 278 nm of 9800$M^{-1}cm^{-1}$ according to the method of Sela & Afinsen, Biochem. Bioiophys. Acta 24:229–235, 1957. This RNase A (5 nM) was mixed with 0.8 to 1.4 equivalents of angiogenin at 25° C. in 0.1 M Mes, pH 6.0, containing 0.1 M NaCl and 1 mM EDTA. PRI was then added to a final concentration of 5nM. After 15 seconds, the activity of free RNase A was then determined by adding CpG (final concentration of 100 $\mu$M) and continuously monitoring the decrease in absorbance at 286 nm on a Varian model 219 spectrophotometer. Angiogenin does not cleave CpG at a detectable rate (Shapiro et al., Biochemistry 25:3527–3532, 1986). The apparent second order rate constant of association was then calculated by using the equation $k_{assoc,A} = k_{assoc,R}\ln([A]_T/[A]_F)/\ln([R]_T/[R]_F)$ where $k_{assoc,R}$ is the apparent second order rate constant of association of PRI with RNase A, $[A]_T$ and $[A]_F$ are the total and free angiogenin concentrations, respectively, and $[R]_T$ and $[R]_F$ are the total and free RNase A concentrations.

The apparent second-order rate constant of association for the Met-(−1)-derivative of the K40R mutant angiogenin was 3.7±0.4 x 10$^8$ $M^{-1}s^{-1}$ at pH 6, 25° C. compared with 4.0±0.3 x 10$^8 M^{-1}s^{-1}$ for the Met-(−1)-derivative of wild-type angiogenin. These association rates with the Met-(−1)-derivatives are ~2.fold higher than for the naturally-occurring <Glu.1 angiogenins.

The K40Q mutant was treated with Aeromonas aminopeptidase to produce the natural pyroglutamyl N-terminus in 95% yield, as determined by Edman degradation. The apparent association rate constant of this mutant with PRI was 6.1x10$^7 M^{-1}s^1$, 3-fold lower than that for native angiogenin.

2. Rate of Dissociation.

The rate constants for the dissociation of the K40R and K40Q mutant angiogenins from their respective complexes with PRI were determined by first forming the complex, then adding a vast excess of RNase A as a scavenger for free PRI, and finally determining the amounts of free angiogenin derivative at various times by cation-exchange HPLC. Final mixtures contained 0.7 μM K40R, K40Q or wild-type angiogenin, 1.0 μM PRI, and 175 μM RNase A in 0.1 M Mes, pH 6.0, wit 0.1 MNAC1, 1 mM EDTA, and 0.12 mM DTT as 25° C. RNase was added after pre-incubation of the remaining components at 25° C. for 20 minutes. At various times, 140 μl aliquots were chromatographed on a Synchropak CM300 HPLC column (250 x 4.1 mm; Synchrom, Inc.) using a 15-minute linear gradient from 0.2 to 0.6 M NaCl in 20 mM sodium phosphate, pH 7.0, at a flow rate of 1 ml/minute. A Waters Associations HPLC system equipped with a 214-nm detector and a Model 730 data module was employed. Free angiogenin was well resolved from the other components and was quantitated by peak area. A control sample lacking PRI, assayed at the end of the experiment, showed that there was no significant loss of angiogenin during the course of the incubation.

Analysis of the dissociation of the K40R-PRI complex as a first-order process yielded a rate constant of $1.4 \times 10^{-5} s^{-1}$, corresponding to a half-life of 14 hours. After 48 hours, ~98% of the angiogenin derivative had been released. This rate is 100.fold faster than for native anigogenin. The rate of dissociation with wild-type [Met-(−1)] angiogenin is indistinguishable from that of the natural protein.

Similar analysis of the K40Q-PRI complex dissociation yielded a dissociation rate constant of $5.7 \times 10^{-5} s^{-1}$, corresponding to a half-life of 3.4 hours. This rate is 440.fold higher than that for the native angiogenin-PRI complex.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A mutated angiogenin protein having the amino acid sequence in FIG. 1, except that the lysine at or corresponding to position 40 has been replaced with another amino acid, said mutated angiogenin protein having decreased angiogenic and ribinucleolytic activity.

2. A DNA sequence comprising a nucleotide sequence encoding a mutated angiogenin protein, which protein has the amino acid sequence in FIG. 1, except that the lysine at or corresponding to position 40 has been replaced with another amino acid, said mutated angiogenin protein having decreased angiogenic and ribonucleolytic activity.

3. A vector comprising a DNA sequence capable of expressing in a transformed bacterial host cell a mutated angiogenin protein having the amino acid sequence in FIG. 1, wherein the lysine at or corresponding to position 40 has been replaced with another amino acid, said mutated angiogenin protein having decreased angiogenic and ribonucleolytic activity.

4. A plasmid identical to A.T.C.C. Deposit No. 67749, said plasmid comprising a DNA sequence capable of expressing in a transformed bacterial host cell a mutated angiogenin protein having the amino acid sequence in FIG. 1, except that the lysine at or corresponding to position 40 has been replaced with glutamine, said mutated angiogenic protein having decreased angiogenic and ribonucleolytic activity.

5. A plasmid identical to A.T.C.C. Deposit No. 67751, said plasmid comprising a DNA sequence capable of expresing in a transformed bacterial host cell a mutated angiogenin protein having the amino acid sequence in FIG. 1, except that the lysine at or corresponding to position 40 has been replaced with glutamine, said mutated angiogenic protein having decreased angiogenic and ribonucleolytic activity.

6. A host cell transformed or transfected to contain and express a nucleotide sequence encoding a mutated angiogenin protein, which protein has the amino acid sequence in FIG. 1, wherein the lysine at or corresponding to position 40 has been replaced with another amino acid, said mutated angiogenin protein having decreased angiogenic and ribonucleolytic activity.

7. A bacterial host cell transformed with a plasmid identical to A.T.C.C. Deposit 67749, said bacterial host cell being capable of expressing a mutated angiogenin protein having the amino acid sequence in FIG. 1, except that the lysine at or corresponding to position 40, has been replaced with arginine, said mutated angiogenin protein having decreased angiogenic and ribonucleolytic activity.

8. A bacterial host cell transformed with a plasmid identical to A.T.C.C. Deposit No. 67751, said bacterial host cell capable of expressing a mutated angiogenin protein having the amino acid sequence in FIG. 1, except that the lysine at or corresponding to position 40, has been replaced with glutamine, said mutated angiogenin protein having decreased angiogenic and ribonucleolytic activity.

9. A mutated angiogenin protein according to claim 1, wherein the amino acid replacing the lysine at or corresponding to position 40 is arginine.

10. A mutated angiogenin protein according to claim 1, wherein the amino acid replacing the lysine at or corresponding to position 40 is glutamine.

11. A DNA sequence according to claim 2, wherein the mutated angiogenin protein encoded by the nucleotide sequence has an arginine at or corresponding to position 40.

12. A DNA sequence according to claim 2, wherein the mutated angiogenin protein encoded by the nucleotide sequence has a glutamine at or corresponding to position 40.

13. A mutated angiogenin protein having the amino acid sequence in FIG. 1, except that the histidine at or corresponding to position 13 or position 114 has been replaced with another amino acid, said mutated angiogenin protein having decreased angiogenic and ribonucleolytic activity.

14. A DNA sequence comprising a nucleotide sequence encoding a mutated angiogenin protein, which protein has the amino acid sequence in FIG. 1, wherein the histidine at or corresponding to position 13 or position 114 has been replaced with another amino acid, said mutated angiogenin protein having decreased angiogenic and ribonucleolytic activity.

15. A vector comprising a DNA sequence capable of expressing in a transformed bacterial host cell a mutated angiogenin protein having the amino acid sequence in FIG. 1, wherein the histidine at or corresponding to position 13 or position 114 has been replaced with another amino acid, said mutated angiogenin protein having decreased angiogenic and ribonucleolytic activity.

16. A plasmid identical to A.T.C.C. Deposit No. 67833, said plasmid comprising a DNA sequence capable of expressing in a transformed bacterial host cell a mutated angiogenin protein having the amino acid sequence in FIG. 1, except that the histidine at or corresponding to position 13 has been replaced with alanine, said mutated angiogenic protein having decreased angiogenic and ribonucleolytic activity.

17. A plasmid identical to A.T.C.C. Deposit No. 67834, said plasmid comprising a DNA sequence capable of expressing in a transformed bacterial host cell a mutated angiogenin protein having the amino acid sequence in FIG. 1, except that the histidine at or corresponding to position 114 has been replaced with alanine, said mutated angiogenic protein having decreased angiogenic and ribonucleolytic activity.

18. A host cell transformed or transfected to contain and express a nucleotide sequence encoding a mutated angiogenin protein, which protein has the amino acid sequence in FIG. 1, wherein the histidine at or corresponding to position 13 or position 114 has been replaced with another amino acid, said mutated angiogenin protein having decreased angiogenic and ribonucleolytic activity.

19. A bacterial host cell transformed with a plasmid identical to A.T.C.C. Deposit No. 67833, said bacterial host cell being capable of expressing a mutated angiogenin protein having the amino acid sequence in FIG. 1, except that the histidine at or corresponding to position 13 has been replaced with alanine, said mutated angiogenin protein having decreased angiogenic and ribonucleolytic activity.

20. A bacterial host cell transformed with a plasmid identical to A.T.C.C. Deposit No. 67834, said bacterial host cell being capable of expressing a mutated angiogenin protein having the amino acid sequence in FIG. 1, except that the histidine at or corresponding to position 114 has been replaced with alanine, said mutated angiogenin protein having decreased angiogenic and ribonucleolytic activity.

21. A mutated angiogenin protein according to claim 13, wherein the amino acid replacing the histidine at or corresponding to position 13 or position 114 is alanine.

22. A DNA sequence according to claim 14, wherein the mutated angiogenin protein encoded by the nucleotide sequence has an alanine at or corresponding to position 13 or 114.

* * * * *